(12) United States Patent
Stohandl et al.

(10) Patent No.: US 7,799,952 B2
(45) Date of Patent: Sep. 21, 2010

(54) STEREOSELECTIVE METHOD FOR THE PRODUCTION OF (R)-DIMEPRANOL

(75) Inventors: Jiri Stohandl, Bobrova (CZ); Jaroslav Frantisek, Brno (CZ); Winfried Ness, Ulm (DE)

(73) Assignee: ratiopharm GmbH, Ulm (DE)

( * ) Notice: Subject to any disclaimer, the term of this patent is extended or adjusted under 35 U.S.C. 154(b) by 0 days.

(21) Appl. No.: 12/368,967

(22) Filed: Feb. 10, 2009

(65) Prior Publication Data

US 2009/0149677 A1    Jun. 11, 2009

Related U.S. Application Data

(62) Division of application No. 11/587,124, filed as application No. PCT/EP2004/013773 on Dec. 3, 2004, now Pat. No. 7,507,827.

(30) Foreign Application Priority Data

Apr. 20, 2004   (EP) .................. 04009280

(51) Int. Cl.
*C07B 57/00*   (2006.01)
(52) U.S. Cl. ...................... 564/503; 564/303
(58) Field of Classification Search .......... 564/303, 564/503
See application file for complete search history.

(56) References Cited

FOREIGN PATENT DOCUMENTS

WO   WO 99/18110   4/1999
WO   WO 03/035652   5/2003

OTHER PUBLICATIONS

Sakai et al., Tetrahedron: Asymmetry 14 (2003) 1631-1636.*

M Cham et al., "Stereoisomeric Lactoyl-β-methylcholine Iodides: Interaction with Cholinesterase and Acetylcholinesterase", J. Med. Chem., vol. 17 (10), pp. 1057-1060 (1974).

\* cited by examiner

*Primary Examiner*—Janet L Andres
*Assistant Examiner*—David E Gallis
(74) *Attorney, Agent, or Firm*—Chalin Smith; Smith Patent Consulting, LLC

(57) ABSTRACT

The present invention relates to processes for preparing a compound of the general formula (Ia)

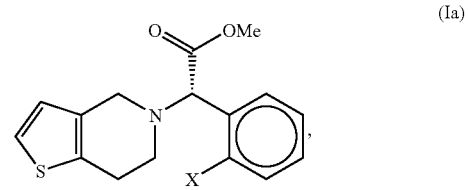

wherein X is a halogen atom, or a pharmaceutically acceptable salt thereof, wherein a compound of the formula (II)

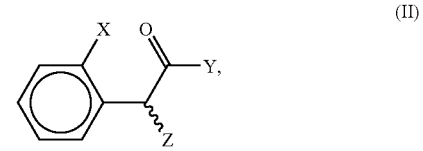

wherein X is as defined above and Y and Z independently represent a leaving group each, is reacted with an optically active amino alcohol to form a first mixture of diastereomers.

1 Claim, No Drawings

STEREOSELECTIVE METHOD FOR THE PRODUCTION OF (R)-DIMEPRANOL

This application is Divisional Application of co-pending U.S. application Ser. No. 11/587,124, filed Oct. 20, 2006, which, in turn, is a Rule 371 U.S. National Phase Filing of PCT/EP04/013773, filed Dec. 3, 2004, which, in turn, claims priority to European Patent Application No. 04.009 280.1, filed on Apr. 20, 2004, the contents of which are incorporated by reference herein in their entirety.

The present invention relates to a stereoselective process for the preparation of optically pure (2-halogenphenyl)(6,7-dihydro-4H-thieno[3,2-c]pyridin-5-yl)acetic acid methyl esters, especially of Clopidogrel, and intermediate compounds for use in this process. This process surprisingly enables the skilled practitioner to obtain the optically pure final compounds more easily and in a better yield.

(2-Halogenphenyl)(6,7-dihydro-4H-thieno[3,2-c]pyridin-5-yl) acetic acid methyl esters and their salts are well known inhibitors of thrombocyte aggregation. In particular, the compound Clopidogrel which, for example, is disclosed in EP-A 99 802 and which has the formula

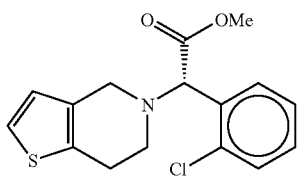

is a highly effective pharmaceutical substance. Clopidogrel is the dextrorotatory compound (+)-[(S)-(2-chlorophenyl)-(6,7-dihydro-4H-thieno[3,2-c]pyridin-5-yl)acetic acid methyl ester which is marketed in the form of the hydrogen sulfate salt.

A number of processes for the preparation of Clopidogrel are well-known. In earlier processes which, for example, are described in EP-A 99 802 and EP-A 420 706, the compound

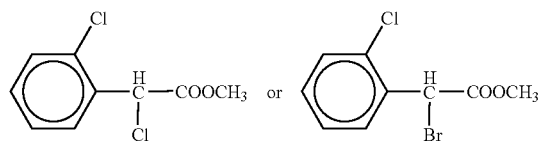

is reacted with the thienopyridine radical

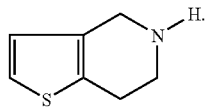

However, these processes were regarded as disadvantageous for subsequent developments and comparatively low yields were achieved under the process conditions indicated.

Accordingly, there are a number of references the subject matter of which is an improvement of the Clopidogrel synthesis. For example, WO 98/51681 discloses a process which proceeds via the open-chained intermediate compounds

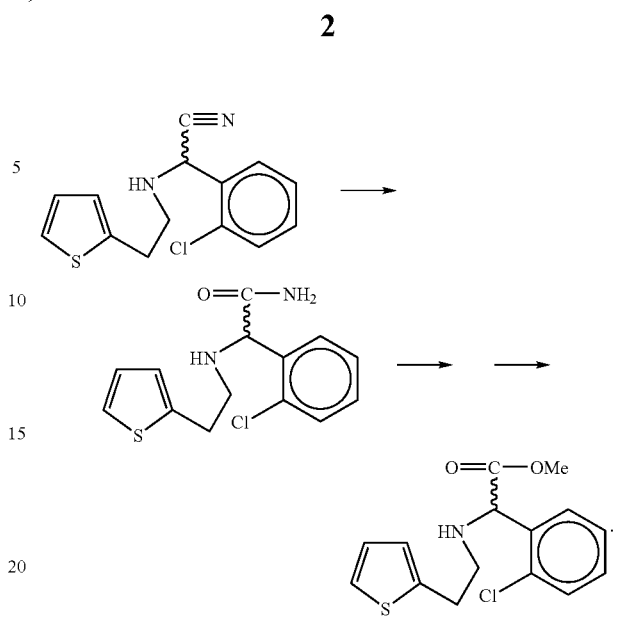

Since the target molecule is a dextrorotatory molecule, the separation of enantiomers is necessary at a certain process stage in all processes for the preparation of Clopidogrel and any subsequent process stages must be carried out with pure enantiomers. In case of the Clopidogrel synthesis, the separation of enantiomers is usually carried out at a comparatively late stage of the process, often only after the last synthesis step, and is fraught with difficulties. Especially if the separation of enantiomers is carried out by reacting a racemic mixture with a compound of pure enantiomers and then precipitating one of the diastereomers formed, selective precipitation often does not occur. Either the desired enantiomer is obtained only in a low yield or with inferior optical purity so that additional purification steps are necessary. Accordingly, an optically contaminated material is often obtained when enantiomers are separated in the examples of WO 98/51681 which requires further work-up to achieve the desired optical purity.

The separation of racemates is particularly difficult if it is carried out on a compound the pyridine ring of which is closed already. Accordingly, the separation of enantiomers according to the process of WO 98/51681 is carried out on an open-chained intermediate, e.g. the intermediate

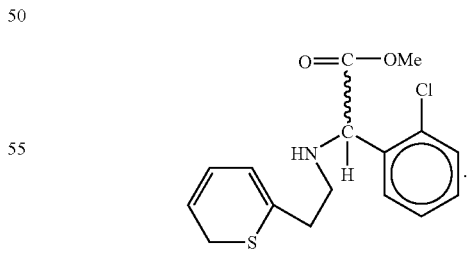

Many more recent processes propose postponing the closure of the pyridine ring to the last process stage after the separation of the enantiomers.

WO 03/035652 discloses a process for the preparation of Clopidogrel which proceeds via the preparation of an intermediate compound of the formula

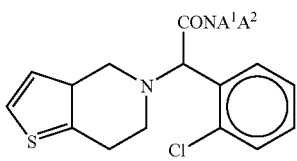

wherein $A^1$ and $A^2$ may independently form hydrogen or $C_1$-$C_4$-alkyl groups or may form a ring. The compound is first prepared as a racemate and then broken down into the individual enantiomers. By the reaction with, for example, methanol and sulfuric acid, Clopidogrel is obtained from the optically active acid amide.

The invention is based on the objective to provide a new synthesis for compounds of the formula

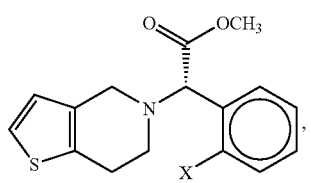 (Ia)

wherein X is a halogen atom, which is both economical and may be carried out in a few stages.

This objective is achieved by a process for preparing a compound of the general formula (Ia)

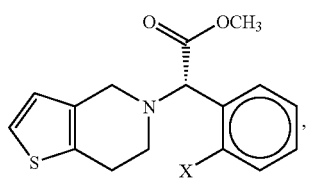 (Ia)

wherein X is a halogen atom, or a pharmaceutically acceptable salt thereof, comprising the process step of reacting a compound of the formula (II)

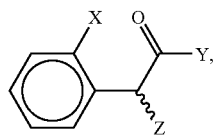 (II)

wherein X is as defined above and Y and Z independently represent a leaving group, with an optically active amino alcohol to form a first mixture of diastereomers.

According to the invention, it was surprisingly found that, in the reaction of the formula (II)

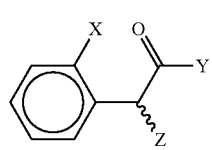 (II)

with an optically active amino alcohol, a first mixture of diastereomers is formed wherein one of the two diastereomers is enriched; in particular, a mixture of diastereomers is formed wherein the ratio of the one diastereomer to the second diastereomer is 2:1 or higher. Preferably, the ratio of the one diastereomer to the other diastereomer is even 3:1 or stereomer to the second diastereomer is 2:1 or higher. Preferably, the ratio of the one diastereomer to the other diastereomer is even 3:1 or higher, especially about 4:1 or higher. According to the invention, it is possible to separate the desired diastereomer even from the first diastereomer mixture and to carry out the ensuing Clopidogrel synthesis with only this one diastereomer. According to the invention, however, it is preferred to process the first diastereomer mixture as such.

Surprisingly, it has also been found that, in the reaction of this first mixture of diastereomers with a compound of the formula (V)

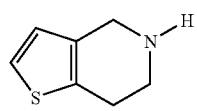 (V)

or with a compound of the formula (VII)

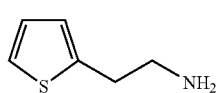 (VII)

a second mixture of diastereomers is formed wherein one of the two diastereomers is enriched even more than in the first mixture of diastereomers. In the second mixture of diastereomers, the ratio of the one diastereomer to the second diastereomer is preferably 3:1 or higher, especially 4:1 or higher, most preferably 9:1 or higher. In a particularly preferred embodiment, the second mixture of diastereomers contains the desired diastereomer in a ratio of 95% or more and the undesirable diastereomer in a ratio of only 5% or less, more preferably the desired diastereomer is present in a ratio of 98% or more and the undesirable diastereomer in a ratio of only 2% or less, and a ratio of the desired diastereomer to the undesirable diastereomer of about 99.5:0.5 or better may be obtained.

The ratio of the desired diastereomer to the undesirable diastereomer in the second diastereomer mixture is preferably higher than in the first diastereomer mixture.

By the appropriate selection of the optical activity of the optically active amino alcohol either the one or the other diastereomer may be obtained in excess.

By the reaction of compound of the formula (II)

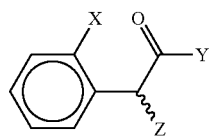

(II)

with an optically active amino alcohol, therefore, a mixture of diastereomers which contains the desired diastereomer in excess may be obtained at a very early stage of the process already. This may then be further reacted to form the compound of the formula (Ia)

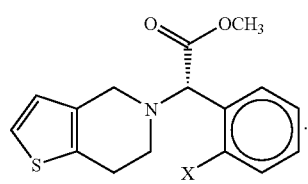

(Ia)

At the end of the reaction, either Clopidogrel in the desired steric arrangement or a mixture of enantiomers wherein the desired enantiomer (Clopidogrel) is already present in high excess is obtained. Either no racemate separation is required or the separation of the racemate may be carried out more easily and with a better yield.

According to the invention, the radical X is a halogen atom, especially a fluorine, chlorine, bromine or iodine atom, especially preferably a chlorine atom.

According to the invention, the radicals Y and Z are common leaving groups as well known in the prior art and described, for example, in Peter Sykes, "Reaktionsmechanismen der organischen Chemie" (Reaction Mechanisms in Organic Chemistry), $9^{th}$ ed., Weinheim 1988. Preferred leaving groups are the halogen atoms, especially iodine, chlorine, bromine or fluorine atoms, a tosylate radical, a triflate radical or a brosylate radical.

The optically active amino alcohol is not particularly limited. Optically active amino alcohols are preferred, wherein at least one optically active centre is arranged close to the hydroxyl group which is coupled to the compound of the formula II, preferably removed from the hydroxyl group by not more than one, two or three bonds.

An optically active amino alcohol of the formula (III)

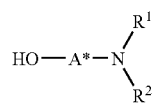

(III)

is especially preferred for use.

Therein

A* represents a hydrocarbon radical with 1 to 30 carbon atoms which may contain up to 5 heteroatoms selected from nitrogen, oxygen, sulfur and halogen atoms and which may be substituted with up to 5 substituents selected from hydroxyl groups, oxo groups, cyano groups and nitro groups and which has one or more optically active units, and $R^1$ and $R^2$ independently represent hydrogen atoms or hydrocarbon radicals with 1 to 20 carbon atoms, each of which may comprise up to 4 hetero atoms selected from nitrogen, oxygen, sulfur and halogen atoms and which may be substituted with up to 5 substituents selected from hydroxyl groups, oxo groups, cyano groups and nitro groups, or one or both of the radicals $R^1$ and $R^2$ form(s) a 5- to 10-membered saturated or unsaturated ring with a carbon atom or a heteroatom of the radical A* which, in addition to the nitrogen atom, may optionally contain 1 to 3 additional hetero atoms selected from nitrogen, oxygen and sulfur atoms as ring members and which may be substituted with up to 5 substituents selected from $C_1$-$C_6$-alkyl radicals, $C_2$-$C_6$-alkenyl radicals, $C_1$-$C_6$-alkoxy radicals, $C_5$-$C_{10}$-aryl radicals (preferably $C_6$-$C_{10}$-aryl radicals), $C_5$-$C_{10}$-heteroaryl radicals, $C_3$-$C_8$-cycloalkyl radicals, $C_2$-$C_8$-heterocycloalkyl radicals, halogen atoms, hydroxyl groups, oxo groups, cyano groups and nitro groups.

The optically active amino alcohols which may be used according to the invention preferably have only a single hydroxyl group so as to avoid competing reactions during the reaction with the compound of the formula (II).

According to the invention, it is preferred that the radicals $R^1$ and $R^2$ independently represent a $C_1$-$C_6$-alkyl radical, a $C_5$-$C_{10}$-aryl radical (preferably a $C_6$-$C_{10}$-aryl radical), a $C_5$-$C_{10}$-heteroaryl radical, a $C_3$-$C_8$-cycloalkyl radical or a $C_2$-$C_8$-heterocycloalkyl radical or, together with the nitrogen atom to which they are bonded, form a saturated or unsaturated ring with 2 to 8 carbon atoms which may optionally be substituted with a $C_1$-$C_6$-alkyl group or a halogen atom and which may contain 1 or 2 additional heteroatoms selected from sulfur atoms, nitrogen atoms and oxygen atoms in addition to the nitrogen atom.

In the present application, an "*" attached to a group of molecules means that this group of molecules is optically active.

In the present application, an "*" attached to a group of molecules means that this group of molecules is optically active.

In the present application, the following radicals are preferred:

Preferred $C_1$-$C_6$-alkyl radicals are methyl, ethyl, isopropyl, n-propyl-, n-butyl, pentyl and hexyl radicals.

Preferred aryl radicals are phenyl or naphthyl radicals, especially phenyl radicals, which may optionally be substituted with 1 to 3 $C_1$-$C_3$-alkyl radicals.

Preferred $C_5$-$C_{10}$-heteroaryl radicals have one or more, preferably 1 or 2, heteroatoms, especially nitrogen, oxygen and/or sulfur atoms. Examples are imidazolyl, oxazolyl, isoxazolyl, thiazolyl, 1,2,3-triazolyl, pyridinyl, pyridazinyl, pyrimidinyl, pyrazinyl and 1-H-pyrazonyl radicals.

Preferred $C_3$-$C_8$-cycloalkyl radicals are cyclopropyl, cyclobutyl, cyclopentyl, cyclohexyl, cycloheptyl and cyclooctyl radicals.

Preferred $C_2$-$C_8$-heterocycloalkyl radicals are cycloalkyl radicals with 2 to 8 carbon atoms which have one or more heteroatoms. Preferred heterocycloalkyl radicals have one or more, preferably 1 or 2, heteroatoms, especially nitrogen, oxygen and/or sulfur atoms. Examples are oxiranyl, aziridinyl, azetidinyl, tetrahydrofuranyl, pyrrolyl and pyranyl radicals.

Preferred $C_2$-$C_6$-alkenyl radicals are ethenyl, propenyl, butenyl and pentenyl radicals.

Preferred $C_1$-$C_6$-alkoxy radicals are methoxy, ethoxy and propoxy radicals, especially methoxy radicals.

Aryl radicals, heteroaryl radicals, cycloalkyl radicals and heterocycloalkyl radicals may be unsubstituted or substituted. If these radicals are substuted, they are preferably substituted with 1 to 3 substituents selected from $C_1$-$C_3$-alkyl, $C_1$-$C_3$-alkoxy radicals and halogen atoms.

Cycloalkyl radicals and heterocycloalkyl radicals may be saturated or unsaturated. Unsaturated radicals preferably have one or two double bonds.

The reaction of the compound of the formula (II)

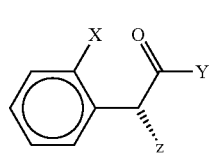
(II)

with the preferred optically active amino alcohol of the formula (III)

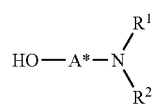
(III)

yields a mixture of the diastereomers (IVa)

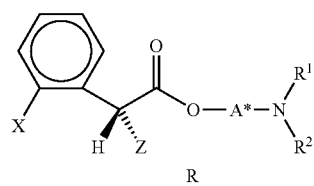
(IVa)

and (IVb)

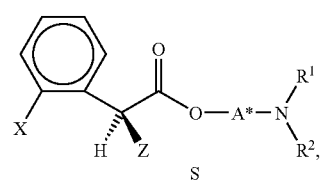
(IVb)

wherein X, Z, A*, $R^1$ and $R^2$ are as defined above. This is called the first diastereomer mixture.

The first diastereomer mixture preferably contains an excess of the diastereomer of the formula (IVa)

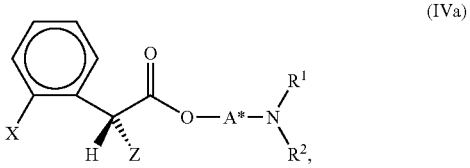
(IVa)

and said excess is generally 2:1 or higher.

The first diastereomer mixture is preferably reacted with the compound of the formula (V)

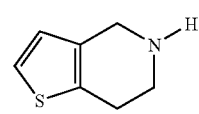
(V)

or the compound of the formula (VII)

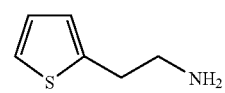
(VII)

resulting in a mixture of diastereomers of the formula (VIa)

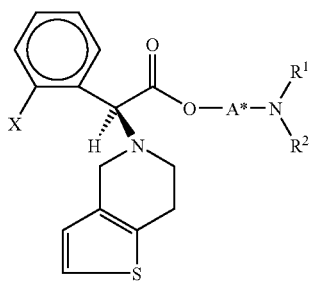
(VIa)

and (VIb)

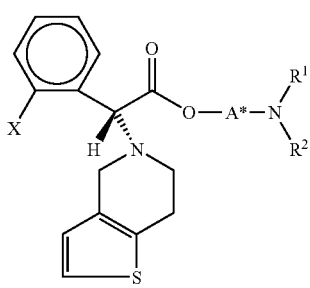
(VIb)

or, respectively, of the formula (VIIIa)

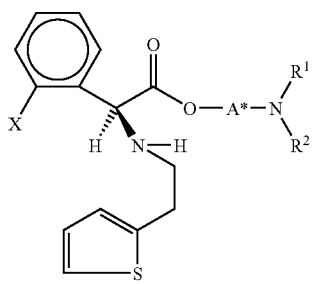

and of the formula (VIIIb)

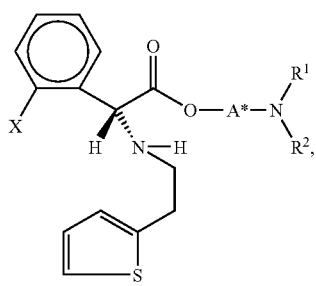

Each of these diastereomer mixtures is called the second diastereomer mixture. The ratio of the diastereomer of the formula (VIa) to the diastereomer of the formula (VIb) or the diastereomer of the formula (VIIIa) to the diastereomer of the formula (VIIIb) is preferably about 3 or more, more preferably about 4 or more and, especially preferably, may be up to 9 or even higher. In a particularly preferred embodiment, the second mixture of diastereomers contains the desired diastereomer in a ratio of 95% or more and the undesirable diastereomer in a ratio of only 5% or less. More preferably the desired diastereomer is present in a ratio of 98% or more and the undesirable diastereomer in a ratio of only 2% or less, and a ratio of the desired diastereomer to the undesirable diastereomer of about 99.5:0.5 or better may be obtained.

In the above formulae, the radicals X, Z, A*, $R^1$ and $R^2$ are as defined above.

In a preferred embodiment, the radical of the formula HO-A* is a radical of the formula

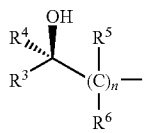

wherein each of the radicals $R^3$ to $R^6$ independently is a hydrogen atom or a hydrocarbon radical with 1 to 20 carbon atoms, each of which may have up to 4 heteroatoms selected from nitrogen, oxygen, sulfur and halogen atoms and may have up to 5 substituents selected from hydroxyl groups, oxo groups, cyano groups and nitro groups, or one or two of the radicals $R^3$ to $R^6$ may form a 5- to 10-membered saturated or unsaturated ring with the radical $R^1$ or the radical $R^2$ which, in addition to the nitrogen atom optionally contains 1 to 3 additional heteroatoms selected from nitrogen, oxygen and sulfur atoms as ring members and which may be substituted with up to 5 substituents selected from $C_1$-$C_6$-alkyl radicals, $C_2$-$C_6$-alkenyl radicals, $C_1$-$C_6$-alkoxy radicals, $C_5$-$C_{10}$-aryl radicals (preferably $C_6$-$C_{10}$-aryl radicals), $C_3$-$C_8$-cycloalkyl radicals, $C_2$-$C_8$-heterocycloalkyl radicals, $C_5$-$C_{10}$-heteroaryl radicals, halogen atoms, hydroxyl groups, oxo groups, cyano groups and nitro groups, and wherein n is an integer from 1 to 3.

In the above formula, it is preferred that the radicals $R^5$ and $R^6$ are independently selected from hydrogen atoms and $C_1$-$C_6$-alkyl radicals, the preferred $C_1$-$C_6$-alkyl radicals being the same as described above. Most preferably, only one of the radicals $R^5$ and $R^6$ is not a hydrogen atom, and in the most preferred embodiment all the radicals $R^5$ and $R^6$ are hydrogen atoms. The index n is preferably 1 or 2, more preferably 1. The radical $R^3$ is preferably a $C_1$-$C_6$-alkyl, $C_1$-$C_6$-alkoxy, $C_5$-$C_{10}$-aryl (preferably a $C_6$-$C_{10}$-aryl), $C_5$-$C_{10}$-heteroaryl, $C_2$-$C_8$-heterocycloalkyl or $C_3$-$C_8$-cycloalkyl radical, it being preferred that the alkyl, alkoxy, aryl, heteroaryl, heterocycloalkyl and cycloalkyl radicals are as defined above. Most preferably, the radical $R^3$ is a $C_1$-$C_6$-Alkyl radical.

It is also preferred for the invention that the radical $R^3$ form a ring with the radical $R^2$, said ring comprising 5 to 10 ring atoms. In addition to the nitrogen atom which the radical $R^2$ is bonded to, this ring comprises 1 to 3 additional heteroatoms selected from oxygen, nitrogen and sulfur atoms and may be saturated or mono- or bi-unsaturated. It may have 1 to 3 substituents selected from $C_1$-$C_6$-alkyl radicals, $C_1$-$C_6$-alkoxy radicals, $C_5$-$C_{10}$-aryl radicals (preferably $C_6$-$C_{10}$-aryl radicals), $C_3$-$C_8$-cycloalkyl radicals, $C_2$-$C_8$-heterocycloalkyl radicals, $C_5$-$C_{10}$-heteroaryl radicals and halogen atoms.

Especially preferably, the radical $R^4$ is a hydrogen atom or a $C_1$-$C_6$-alkyl radical, most preferably a hydrogen atom.

The radicals $R^3$ and $R^4$ are preferably different so that the optically active centre is located on the carbon atom which also bears the hydroxyl groups. However, the radicals $R^3$ and $R^4$ may be the same, too, e.g. both may be hydrogen atoms, and the optically active centre may be located on another carbon atom which is due to the fact that the radicals $R^5$ and $R^6$ are different on this carbon atom. It is preferred to select the substitution pattern in such a way that the above-mentioned radical HO-A*, namely

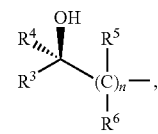

is present in the R configuration, because this results in diastereomer mixtures in subsequent reaction steps where the relevant diastereomer which yields Clopidogrel in the desired steric configuration is present in excess.

If the compound of the formula (II) is reacted with an optically active amino alcohol of the formula (III) which is preferred for the invention, a first mixture of diastereomers of the formula (IVa)

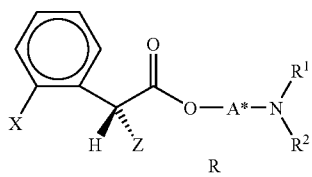

and of the formula (IVb)

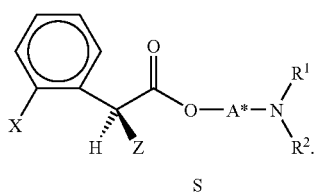

results.

For the especially preferred embodiment, wherein the radical HO-A* is a radical of the formula

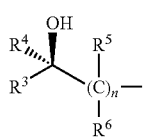

a diastereomer mixture of the compounds of the formula

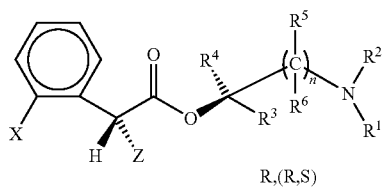

and

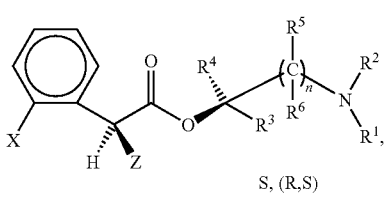

results wherein the radicals X, Z, $R^1$ to $R^6$ and the index n are as defined above. This is called the first diastereomer mixture.

If an optically active amino alcohol having the following steric configuration (in the R-configuration)

is used in the invention, the R,(R,S) compound of the formula (IVa-1) is formed in excess vis-à-vis the S,(R,S)-compound of the formula (IVb-1), and the ratio between the R,(R,S)- and the S,(R,S)-compound is preferably 2:1 or higher, more preferably 3:1 or higher and especially about 4:1 or higher.

In the invention, it is possible to separate the enantiomers already in the first diastereomer mixture and to continue the further Clopidogrel synthesis with only the R,(R,S)-diastereomer of the formula (IVa-1). The separation of the diastereomers may be carried out in a manner known per se, for example by crystallisation or by a chromatographic process. It is preferred for the invention, however, to react the first diastereomer mixture as such with a compound of the formula

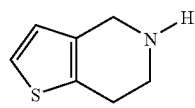

or with a compound of the formula (VII)

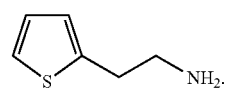

Such a reaction with the compound of the formula (V)

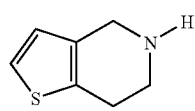

yields the following mixture of diastereomers

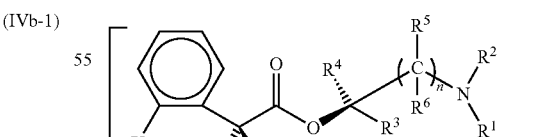
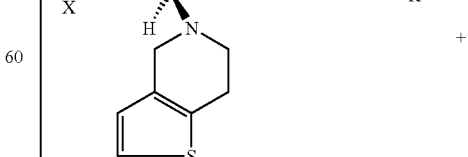

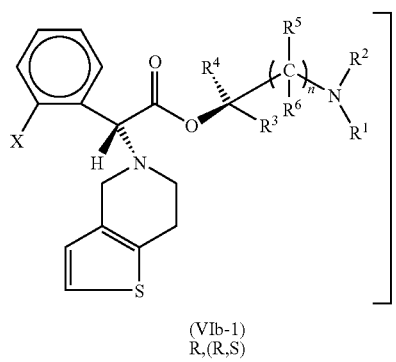

(VIb-1)
R,(R,S)

wherein the radicals X, $R^1$ to $R^6$ and the index n are as defined above. This is called the second diastereomer. It is a mixture of the diastereomers

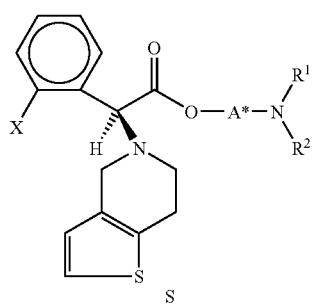

(VIa)

and

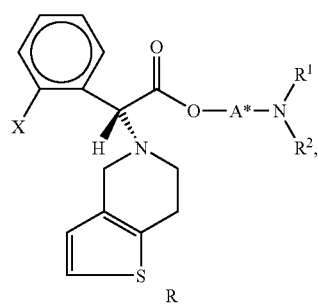

(VIb)

wherein the radical —O-A* is a radical of the formula

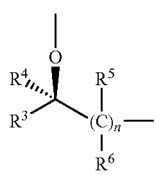

The S,(R,S)-compound of the formula (VIa-1) is preferably present in excess vis-à-vis the R,(R,S)-compound of the formula (VIb-1). Surprisingly, the diastereomeric excess has increased yet again as a result of the reaction with the compound of the formula (V)

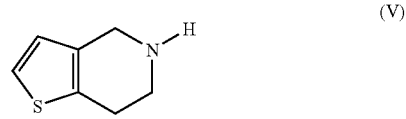

(V)

so that the ratio of the compound of the formula (VIa-1) to the compound of the formula (VIb-1) is preferably 3:1 or higher, more preferably 4:1 or higher. In the most preferred embodiment of the invention, even a ratio of the diastereomers of 9:1 or higher is achieved. In a particularly preferred embodiment, the second diastereomer mixture contains the desired diastereomer in a ratio of 95% or more and the undesirable diastereomer in a ratio of only 5% or less. More preferably, the desired diastereomer is present in a ratio of 98% or more and the undesirable diastereomer in a ratio of only 2% or less, and a ratio of the desired diastereomer to the undesirable diastereomer of about 99.5:0.5 or better may be obtained.

If the mixture of diastereomers (first diastereomer mixture)

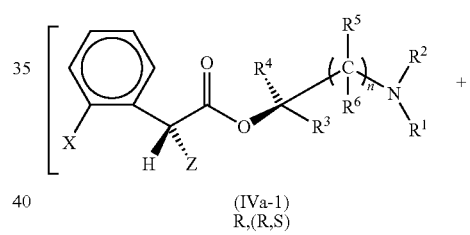

(IVa-1)
R,(R,S)

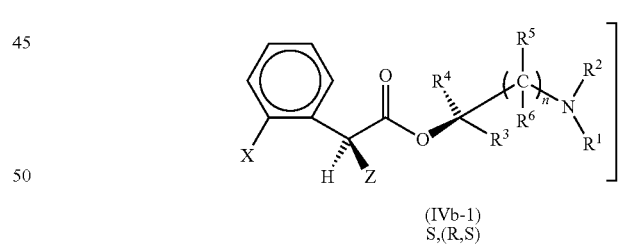

(IVb-1)
S,(R,S)

is reacted with a compound of the formula (VII)

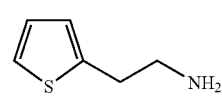

(VII)

a mixture of the diastereomers (second diastereomer mixture) is formed accordingly:

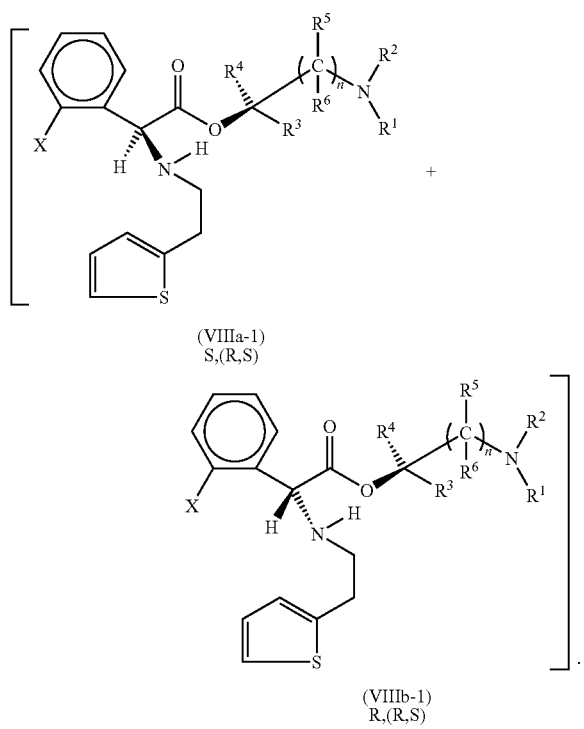

(VIIIa-1)
S,(R,S)

(VIIIb-1)
R,(R,S)

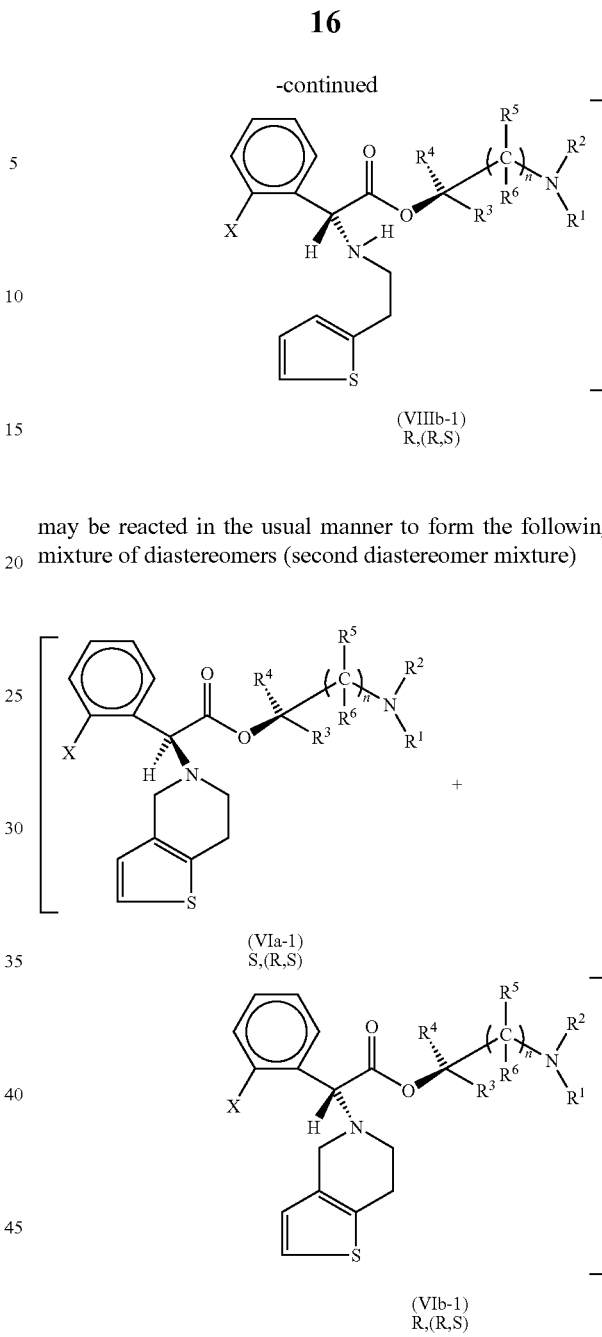

(VIIIb-1)
R,(R,S)

may be reacted in the usual manner to form the following mixture of diastereomers (second diastereomer mixture)

(VIa-1)
S,(R,S)

(VIb-1)
R,(R,S)

In this diastereomer mixture, the diastereomer S,(R,S) of the formula (VIIIa-1) is preferably present in excess vis-à-vis the diastereomer R,(R,S) of the formula (VIIIb-1) (provided the "correct" enantiomer of the amino alcohol is used; otherwise the ratio of the diastereomers is the other way round). Again, the excess of the diastereomer of the formula (VIIIa-1) vis-à-vis the diastereomer of the formula (VIIIb-1) is surprisingly increased and is preferably 3:1 or higher, more preferably 4:1 or higher or even 9:1 or higher. In a particularly preferred embodiment, the second mixture of diastereomers contains the desired diastereomer in a ratio of 95% or more and the undesirable diastereomer in a ratio of only 5% or less. More preferably, the desired diastereomer is present in a ratio of 98% or more and the undesirable diastereomer in a ratio of only 2% or less, and a ratio of the desired diastereomer to the undesirable diastereomer of about 99.5:0.5 or better may be obtained.

The mixture of the following diastereomers (second diastereomer mixture)

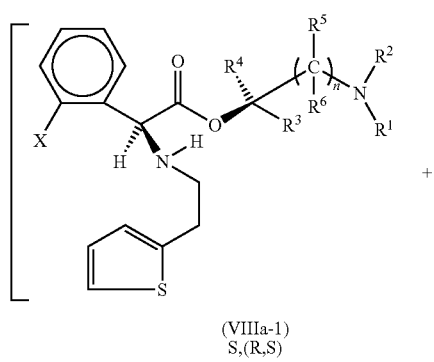

(VIIIa-1)
S,(R,S)

as generally known in the prior art.

As far as this reaction is concerned, please refer to the publications discussed in the introductory part and the following observations on the ring-closure reaction of the tetrahydrothienopyridine.

The most preferred optically active amino alcohol is (R)-1-(dimethylamino)-2-propanol ((R)-Dimepranol). This optically active amino alcohol is available commercially, but in connection with the invention it was found that it may be obtained easily by the optical resolution of the relevant racemic amino alcohol with di-O-benzoyl-L-(−)-tartaric acid. This increases the profitability of the process of the invention. Other optically active alcohols that may be used in the process of the invention may also be recovered from the relevant racemic alcohol in this manner.

With the optically active amino alcohol (R)-Dimepranol preferred for the invention, the following formulae result for the first diastereomer mixture and the second diastereomer mixture:

First diastereomer mixture:

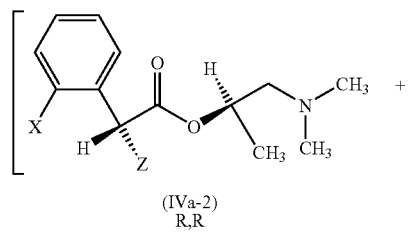

(IVa-2)
R,R

+

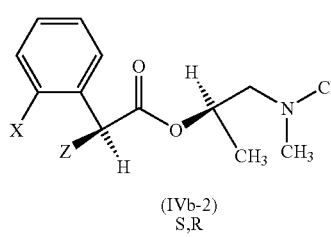

(IVb-2)
S,R

Second diastereomer mixture:

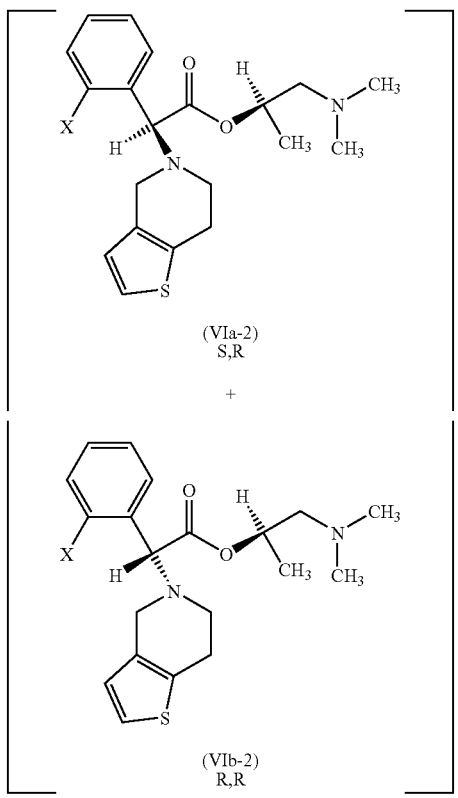

or, respectively, with the open-chained compound:

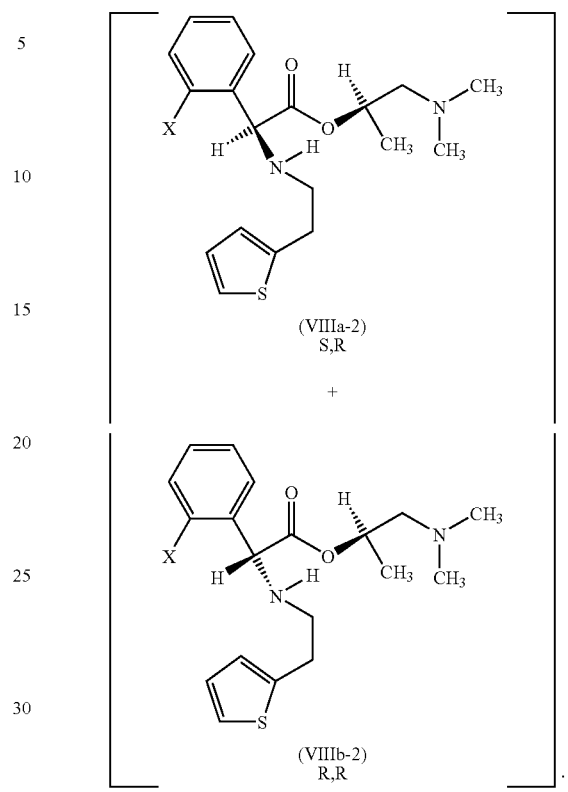

Additional optically active amino alcohols preferred for the invention are the compounds of the formulae (shown below without indication of the stereochemistry):

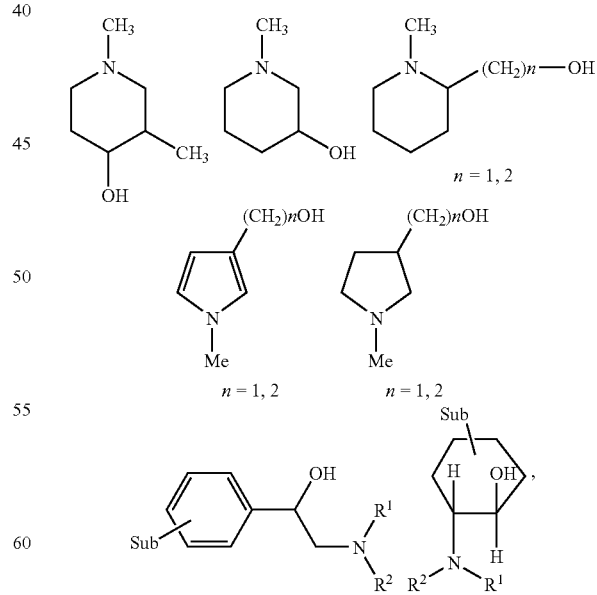

wherein the radicals $R^1$ and $R^2$ are as defined above and "Sub" means that the ring may be substituted with a $C_1$-$C_3$-alkyl radical at any location.

The compounds

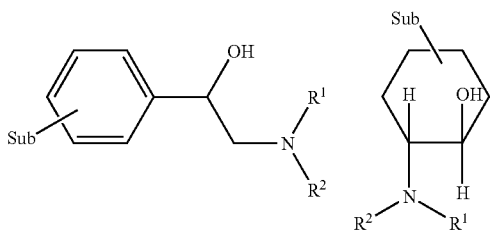

may be prepared easily from substituted styrene oxide or substituted cyclohexene oxide and separated into their individual enantiomers as described in "Optical Resolution via Diastereoisomeric Salts Formation", David Kozma, Ed., CRC Press, London, New York, Washington D.C.

In the invention, it is also preferred that the radical HO-A* is a radical of the formula

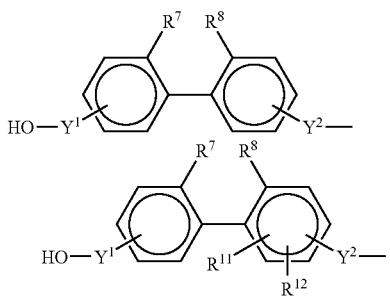

or wherein $Y^1$ is a radical

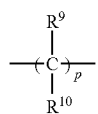

and $Y^2$ is a radical

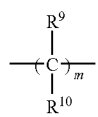

wherein $R^9$ and $R^{10}$ are independently selected from hydrogen atoms and $C_1$-$C_6$-alkyl radicals and the radicals $R^7$ and $R^8$ are groups preventing free rotatability of the two phenyl groups relatively to each other, $R^{11}$ and $R^{12}$ independently are hydrogen atoms, $C_1$-$C_4$-alkoxy radicals, halogen atoms, cyano radicals, $C_1$-$C_6$-alkoxycarbonyl radicals or $C_1$-$C_6$-alkyl radicals, or $R^{11}$ and $R^{12}$, together with the benzene ring to which they are bonded, form a condensed ring structure which is selected from a 1,3-benzodioxolyl, α-naphthyl, β-naphthyl, tetrahydronaphthyl, benzimidazolyl and benztriazolyl structure, m is an integer from 0 to 2 and p is 1 or 2.

Especially preferably, all of the radicals $R^9$ and $R^{10}$ are hydrogen atoms or only one radical is not a hydrogen atom and is a $C_1$-$C_6$-alkyl radical, preferably a $C_1$-$C_3$-alkyl radical.

Especially preferably, one of the radicals $R^7$ and $R^8$ is selected from a $C_1$-$C_6$-alkyl group, a halogen atom and a cyano group, and the second radical is selected from a $C_3$-$C_6$ branched alkyl group, preferably a tertiary butyl group, a halogen atom and a cyano group. High-volume halogen atoms such as iodine atoms are preferred.

In this radical, optical activity is generated by at least one of the radicals $R^7$ and $R^8$, preferably both radicals $R^7$ and $R^8$, being high-volume radicals such as alkyl groups (especially a branched $C_3$-$C_6$-Alkyl group), halogen atoms or cyano groups so that rotation of the two phenyl rings is prevented.

In another embodiment preferred for the invention, the compound of the formula

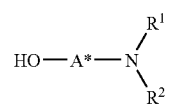

is a compound of the formula

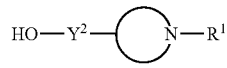

wherein $Y^2$ is as defined above, $R^1$ is as defined above and preferably is a hydrogen atom or a hydrocarbon radical with 1 to 20 carbon atoms which may contain up to 4 heteroatoms selected from nitrogen, oxygen, sulfur and halogen atoms and up to 5 substituents selected from hydroxyl groups, oxo groups, cyano groups and nitro groups and the group

is a 5- to 10-membered saturated or unsaturated ring which, in addition to the nitrogen atom, optionally contains 1 to 3 hetero atoms selected from nitrogen, oxygen and sulfur atoms as ring members and which may be substituted with up to 5 substituents selected from $C_1$-$C_6$-alkyl radicals, $C_1$-$C_6$-alkoxy radicals, $C_2$-$C_6$-alkenyl radicals, $C_5$-$C_{10}$-aryl radicals (especially $C_6$-$C_{10}$-aryl radicals), $C_5$-$C_{10}$-heteroaryl radicals, $C_3$-$C_6$-cycloalkyl radicals, $C_2$-$C_8$-heterocycloalkyl radicals, halogen atoms, hydroxyl groups, oxo groups, cyano groups and nitro groups.

Preferably, the group

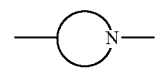

is a group

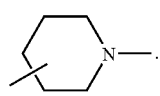

The reaction products of the above-mentioned optically active amino alcohols with the compounds of the formula (II) to form the first diastereomer mixture and the reaction products of the first diastereomer mixture with a compound of the formula (V)

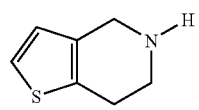
(V)

or a compound of the formula (VII)

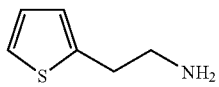
(VII)

to form the second diastereomer mixture are novel compounds, and the invention also relates to the corresponding diastereomer mixtures with any desired ratios of the individual diastereomers and the individual isolated diastereomers from these diastereomer mixtures.

The further processing of the second diastereomer mixture to obtain the final product of the formula (Ia)

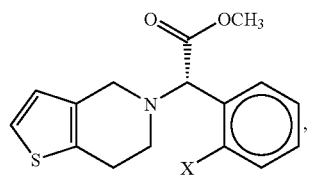
(Ia)

especially Clopidogrel

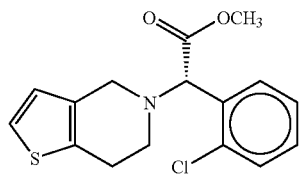

is carried out in a manner known per se to the skilled practitioner. The following process sequences are possible in general, the following formulae being shown with the preferred optically active amino alcohol of the formula (III)

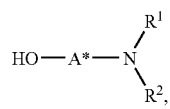
(III)

but other amino alcohols may also be used. In particular, the other amino alcohols mentioned in the application may be used.

If a mixture of diastereomers of the formula (VIIIa)

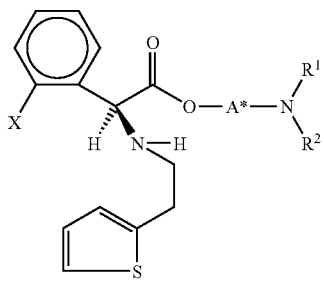
(VIIIa)

and (VIIIb)

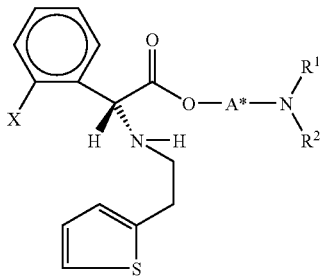
(VIIIb)

is present, either a ring closure reaction to form a mixture of diastereomers of the formulae (VIa)

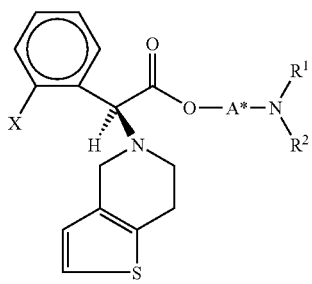
(VIa)

and (VIb)

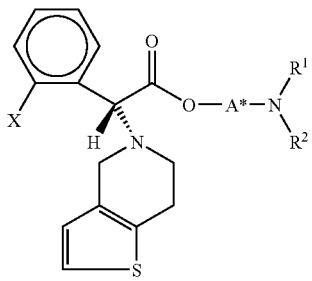
(VIb)

may first be carried out. This mixture is then further reacted as described below. It is also possible to first carry out a separation of diastereomers in the mixture of diastereomers (VIIIa)

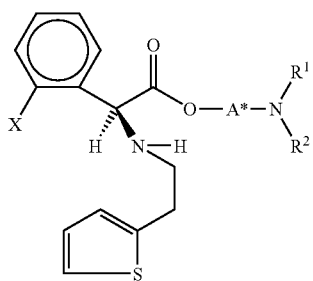
(VIIIa)

and (VIIIb)

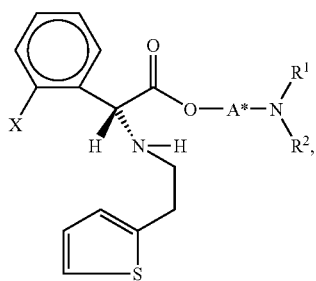
(VIIIb)

for example by crystallisation (preferred) or by a chromatographic process and to subject only the diastereomer of the formula (VIIIa)

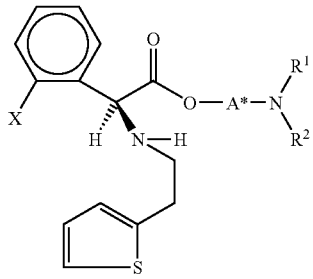
(VIIIa)

to a further reaction. The individual diastereomer of the formula (VIIIa)

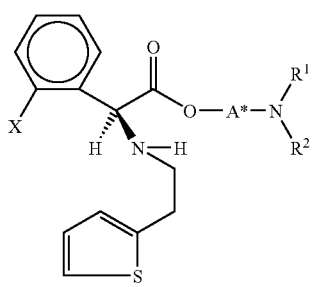
(VIIIa)

may then either be converted first into a the compound of the formula (VIa)

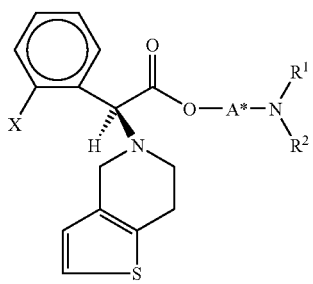
(VIa)

by a ring closure reaction with the stereochemistry being maintained as shown for similar compounds in the prior art and then subjected to trans-esterification as shown below. Alternatively, the compound of the formula (VIIIa) may first subjected to transesterification to provide the compound of the formula

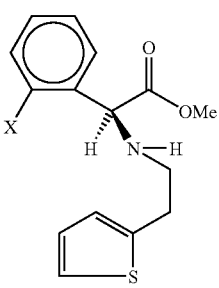

which is then converted to the compound of the formula (Ia)

(Ia)

preferably Clopidogrel by ring closure as described in the prior art, for example in EP 466 569.

The second diastereomer mixture with diastereomers of the formulae (VIa)

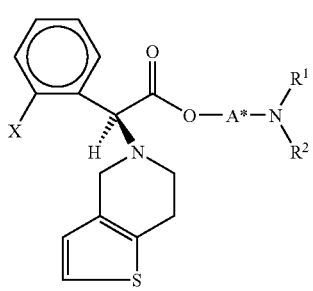
(VIa)

and (VIb)

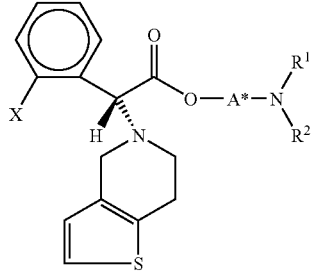
(VIb)

the chains of which have already been closed, wherein the diastereomer of the formula (VIa)

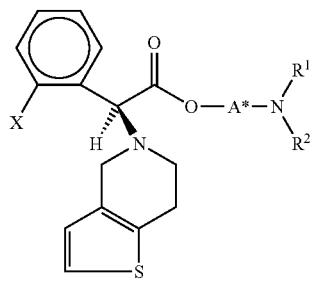
(VIa)

is preferably present in a excess of at least 3:1 or more, more preferably 4:1 or more, most preferably 9:1 or more (or wherein the second mixture of diastereomers contains the desired diastereomer in a ratio of 95% or more and the undesirable diastereomer in a ratio of only 5% or less, more preferably wherein the desired diastereomer is present in a ratio of 98% or more and the undesirable diastereomer in a ratio of only 2% or less, and especially wherein the ratio of the desired diastereomer to the undesirable diastereomer is about 99.5:0.5 or better) may either be subjected to a diastereomer separation first, which is preferred for the invention. As a result, the diastereomer of the formula (VIa)

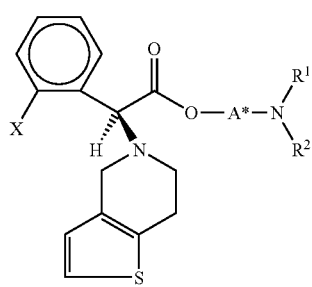
(VIa)

is separated. The diastereomer separation may be carried out in a manner known per se and described in the prior art and, in greater detail, in the examples. Then the diastereomer of the formula (VIa)

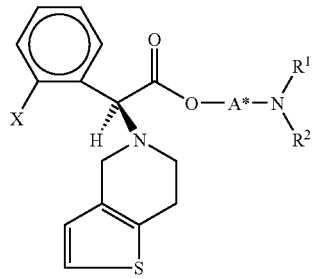
(VIa)

is subjected to a transesterification reaction maintaining the stereochemistry to obtain the compound of the formula (Ia)

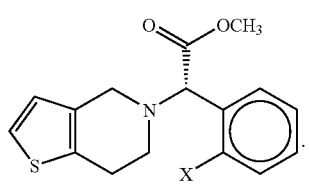
(Ia)

Alternatively, the diastereomer mixture of the compounds of the formula (VIa)

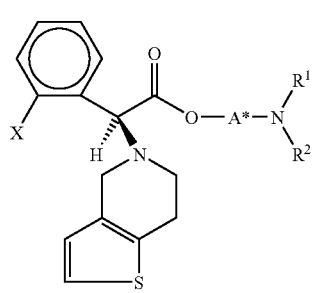
(VIa)

and (VIb)

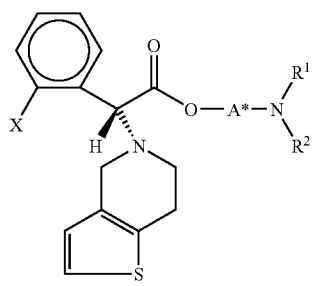
(VIb)

may be subjected to a transesterification reaction without prior separation. This variation is especially preferred if a very high excess of the diastereomer of the formula (VIa)

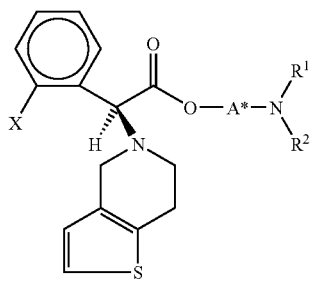

is present or if the subsequent transesterification cannot be completed with the stereochemistry being maintained. The transesterification then results in a mixture of the compounds (Ia)

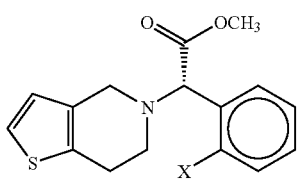

and (Ib)

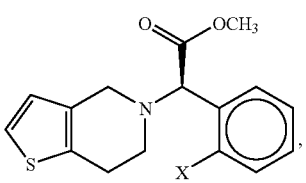

wherein, however, the compound (Ia) is present in considerable excess vis-à-vis the compound of the formula (Ib). If necessary, this mixture of enantiomers may then be subjected to a separation of enantiomers as well known in the prior art.

The transesterification is preferably carried out using a titanium or silicon catalyst, especially preferably using a titanium(IV) alkoxide, in particular a titanium(IV) isopropoxide (tetraisopropylorthotitanate) or a titanium(IV) ethoxide as commercially available from the Fluka Company, for example. The titanium alkoxide is activated by the reaction with a suitable alcohol, e.g. with ethylene glycol. Another catalyst may be used, too, for example chlorinated silica, as may be obtained, for example, by the reaction of silica with thionyl chloride, optionally in phosphorus pentachloride or by the reaction of silica with only phosphorus pentachloride in a suitable inert solvent such as hexane, chloroform, chlorobenzene or dichlormethane.

In a particularly preferred embodiment which is especially advantageous if the diastereomer mixture already has a very high excess of the desired diastereomer, the transesterification is carried out using a halide of a transition metal of the first or second sub-group of the periodic table of elements. Suitable catalysts are, for example, $ZnX_2$, $Cu_2X_2$, $CuX_2$, $AgX$, $AuX$, $AuX_3$, $CdX_2$, $Hg_2X_2$, $HgX_2$, $CoX_2$, X representing the halide counter ion, especially a fluoride, chloride, bromide or iodide ion, in particular a chloride ion. Most preferably, the transition metal is zinc or cobalt so that the most preferable catalyst of the invention is $ZnX_2$ or $CoX_2$.

In general, halides of other metals of the $3^{rd}$ to $8^{th}$ transition metal group of the periodic table of elements may also be used, but, as a rule, these require an acidic medium which increases the risk of racemisation. Also, their catalytic characteristics are often poorer so that these catalysts are not preferred for the invention.

It is a particular advantage of the transition metal halide catalysts, especially of zinc chloride, that the reaction may be carried out under alkaline conditions and that, if at all, racemisation during transesterification occurs only to a very small degree. For example, if one of the particularly preferred second diastereomer mixtures of the invention which contains the desired diastereomer in a ratio of 98% or more, more preferably 99% or more and the undesirable diastereomer in a ratio of only 2% or less, especially 1% or less is used for the transesterification, diligent process control will yield a product after transesterification which contains 80% or more, especially 90% or more, preferably about 95% or more, more preferably about 98% or more, of the desired enantiomer of the formula (Ia)

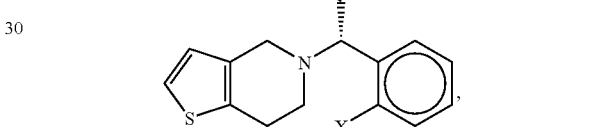

(i.e. of the Clopidogrel when X is Cl), the remainder being the undesirable enantiomer of the formula (Ib)

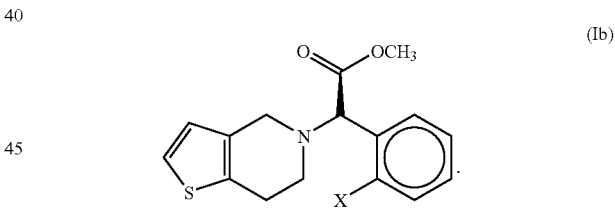

Additional purification of the Clopidogrel mixture to increase the ratio of the desired enantiomer of the formula (Ia)

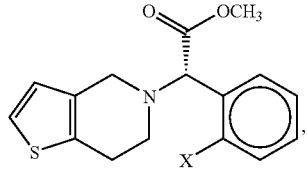

namely the Clopidogrel, may be achieved by treatment with an acid as shown in the examples.

In general, transesterification may also be carried out without using a catalyst. In that case, however, longer reaction times must be accepted.

In order to effect transesterification, it is most advantageous to work in methanol as the solvent, because the objective is the preparation of a methyl ester.

Below, the process of the invention is illustrated in greater detail using the example of the reaction of 2-chlorophenyl acetic acid with (R)-Dimepranol and the subsequent reaction with 2-(2-thienyl)ethyl amine. However, the reaction will proceed accordingly if another optically active amino alcohol is used instead of the (R)-Dimepranol or if another 2-halogen phenyl acetic acid is used instead of 2-chlorophenyl acetic acid and if the pertinent open-chained compound which is then subjected to a ring closure reaction in a subsequent process step is used instead of the 2-(2-thienyl)ethyl amine.

In general, the reaction proceeds according to the following reaction scheme:

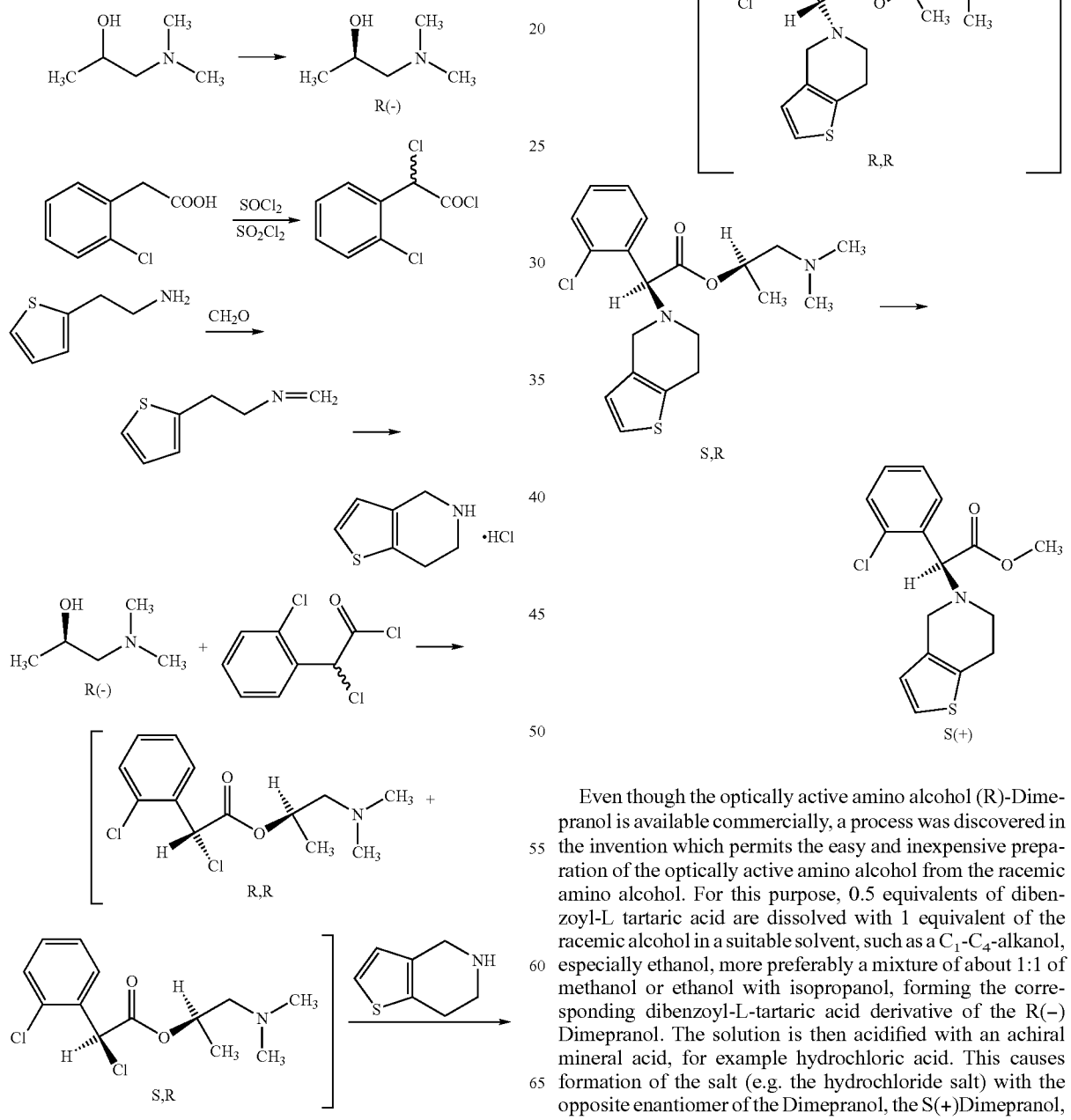

Even though the optically active amino alcohol (R)-Dimepranol is available commercially, a process was discovered in the invention which permits the easy and inexpensive preparation of the optically active amino alcohol from the racemic amino alcohol. For this purpose, 0.5 equivalents of dibenzoyl-L tartaric acid are dissolved with 1 equivalent of the racemic alcohol in a suitable solvent, such as a $C_1$-$C_4$-alkanol, especially ethanol, more preferably a mixture of about 1:1 of methanol or ethanol with isopropanol, forming the corresponding dibenzoyl-L-tartaric acid derivative of the R(−) Dimepranol. The solution is then acidified with an achiral mineral acid, for example hydrochloric acid. This causes formation of the salt (e.g. the hydrochloride salt) with the opposite enantiomer of the Dimepranol, the S(+)Dimepranol, which is kept in solution as a result. After optional seeding, the dibenzoyl-L-tartaric acid derivative of the R(−)Dimepranol precipitates as a crystalline product while the salt of the S(+)Dimepranol remains in solution. The free (R)-Dimepranol base may be recovered from the precipitated salt in a manner known per se by the reaction with a suitable base such as sodium or potassium hydroxide in a suitable solvent such as an alcohol, especially in ethanol. In an alternative embodiment, the dibenzoyl-L-tartaric acid derivative of the R-Dimepranol may, for example, also be converted to the R-Dimepranol hydrochloride by treatment with dry hydrogen chloride. This may then be used as such or after treatment with a suitable base in the alkaline form.

Thanks to the process of the invention, the required quantity of dibenzoyl-L-tartaric acid is reduced, which makes the process very economical. In addition, the product obtained is of high optical purity and repeated recrystallisations are generally not necessary.

2,α-Dichlorophenyl acetyl chloride

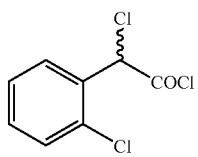

may be prepared in a manner known per se, for example by the following reaction scheme:

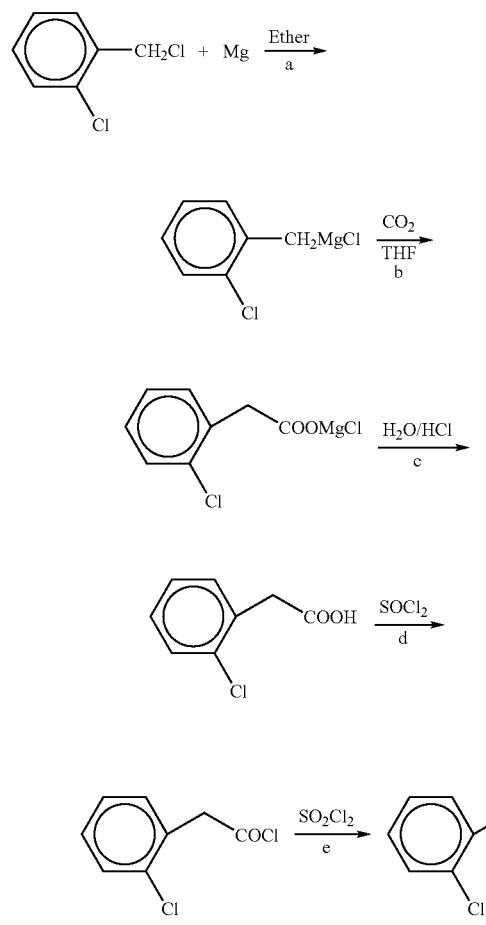

Step (a) is carried out by the reaction of the compound

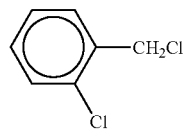

with metallic magnesium in a suitable solvent such as, for example, ether (i.e. diethyl ether), dibutyl ether or a higher ether, THF or another cyclic ether, toluene etc., preferably ether, at reflux. This is a common Grignard reaction. In step (b), an intermediate $CO_2$, preferably in the form of dry ice, may be added to the reaction mixture with vigorous stirring either without a solvent or, preferably, with a solvent capable of dissolving $CO_2$ such as THF. Gaseous carbon dioxide escapes, and the compound

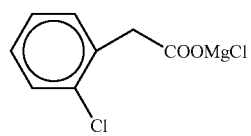

is obtained. After that, hydrolysis is carried out in step (c). For this purpose, diluted mineral acid such as diluted hydrochloric acid is added to the reaction mixture obtained in step (b) with cooling and stirring, resulting in a 2-phase mixture. By adding a suitable base, for example an aqueous base such as a $NH_4OH$ solution in water or an alkalicarbonate solution or ammonium carbonate solution in water, neutralisation is then carried out, yielding an aqueous solution of the salt of the halogenphenyl acetic acid. If necessary, additional water may be added. The organic phase is then separated, and the aqueous phase containing the salt of the 2-halogenphenyl acetic is mixed with, for example, diluted mineral acid until the desired 2-halogenphenyl acetic acid, especially the 2-chlorophenyl acetic acid is precipitated.

The acid is separated and worked up in a suitable manner, for example by dissolution in a suitable solvent such as chloroform, extraction with water, drying of the chloroform phase with sodium sulfate or magnesium sulfate and evaporation of the solvent. By this process, 2-halogen phenylacetic acid is obtained in a favourable yield with a purity of 95% or higher, especially 98% or higher.

The 2-halogenphenyl acetic acid is converted to the acid chloride in the usual manner, for example, as shown in step (d), dissolved in thionyl chloride with heating, resulting in the compound of the formula

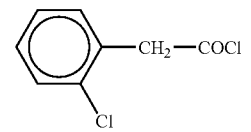

being obtained.

Depending on the desired radical Y, bromination or chlorination is then carried out in step (e). Bromination may be effected by adding liquid bromine in the presence of red phosphorus with heating until reflux. The reaction mixture is left to stand over night, and then the unreacted thionyl chloride and bromine are evaporated, yielding the compound of the formula

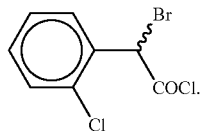

For the preparation of the chlorinated compound, sulfuryl chloride ($SO_2Cl_2$) is added to the reaction mixture with stirring and heating in step (e). Then the remainders of $SOCl_2$ and $SO_2Cl_2$ are evaporated, yielding the compound of the formula

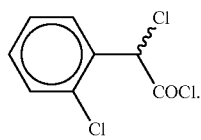

The compound of the formula

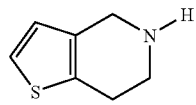

resp. of the formula

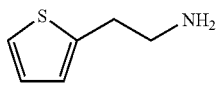

may be obtained in a manner known per se, for example according to the following reaction scheme:

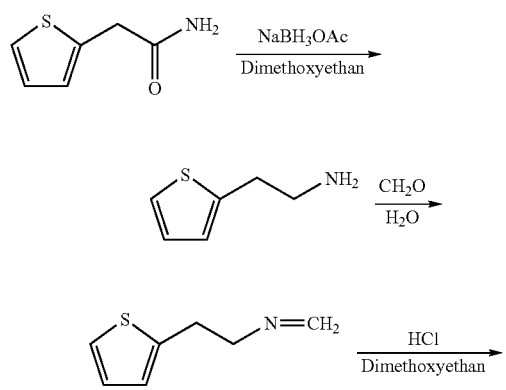

For example, the starting compound 2-thienyl acetamide may be prepared from 2-thienyl acetonitrile or 2-thienyl acetyl chloride in a well known manner. For example, dimethoxy ethane is added to the 2-thienyl acetamide with cooling with sodium borohydride. Then acetic acid is added with additional cooling and stirring. This mixture is heated with stirring and a hydrolysis carried out with the addition of water, cooling being optional. After evaporation of the dimethoxy ethane, the solution is basified, for example by adding a suitable base such as potassium hydroxide or sodium hydroxide, and a suitable solvent such as ether is added. The aqueous phase is separated. The organic phase is washed, acidified, for example with a mineral acid, and subjected to extraction once more. The organic phase is separated. The aqueous phase is basified, for example by adding potassium hydroxide or sodium hydroxide, and ether is added. The organic phase contains the desired 2-(2-thienyl)ethyl amine, and after evaporation of the solvent the 2-(2-thienyl)ethyl amine is obtained with a purity of preferably 95% or higher, more preferably 98% or higher.

The 2-(2-thienyl)ethyl amine thus obtained may be heated with stirring, for example with aqueous formaldehyde. This is followed by cooling, and a suitable organic solvent such as dichloromethane is added. After addition of a base, for example sodium hydroxide or potassium hydroxide, such as a 10% sodium hydroxide solution, an extraction is carried out. The aqueous phase is separated, and the organic phase is evaporated until dry. The residue is dissolved, for example in dimethoxy ethane, and acidified. This is followed by cyclisation with a Schiff base with stirring. After cooling, filtration and washing, the desired 4,5,6,7-tetrahydro[3,2-c]thienopyridine is obtained.

This reaction for preparation of the compound

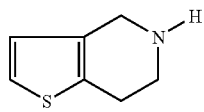

is, for example, also described in EP-A 439 404 and in Arkiv för kemi, 32, (19), 217-227 (1971). Reference is made to the entire contents of these publications.

The starting compounds of the syntheses are well known to the skilled practitioner and may either be obtained commercially or prepared easily by processes known from literature.

The reaction of the compound of the formula (II)

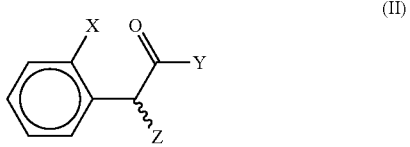

with the compound of the formula (III)

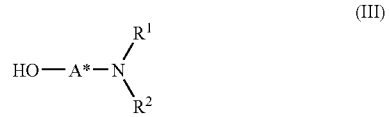

is carried out in a manner known per se. For example, 2,α-dichlorophenyl acetyl chloride is reacted with (R)-1-(dimethylamino)-2-propanol in a suitable solvent, especially in a dipolar aprotic solvent, e.g. an ether such as THF, preferably in the presence of an amine such as a pyridine compound like 4-(dimethylamino)pyridine and especially in the presence of a tertiary amine like triethyl amine. The crystalline hydrochloride of the resulting amino ester precipitates and may be separated. In a particularly preferred embodiment, the mixture is first heated at reflux with a suitable ketone, especially with acetone, which increases the content of the desired R,R-diastereomer. Therefore, this embodiment is particularly advantageous to achieve a high excess of the desired diastereomer at a very early stage of the process.

If a tertiary amine such as triethyl amine is used for the preparation of the first diastereomer mixture, the filtered crystalline product contains a mixture of the desired diastereomer mixture and triethyl amine. Due to the fact that the diastereomer mixture also contains a tertiary amine, it may usually be filtered off more easily and, surprisingly, racemisation in the subsequent process step for the preparation of the second diastereomer mixtures is reduced.

The work-up and, optionally, purification is conducted in a well known manner, for example by recrystallisation and/or chromatography. Often, it is possible to process the crude mixture directly. The solvents suitable for use are not particularly limited, but no primary alcohols such as methanol or ethanol should be used to avoid the risk of transesterification. Secondary alcohols or tertiary alcohols such as 2-propanol may be used; especially for recrystallisation, the use of such secondary alcohols like 2-propanol may be advantageous.

The ratio of the two diastereomers in the resulting mixture

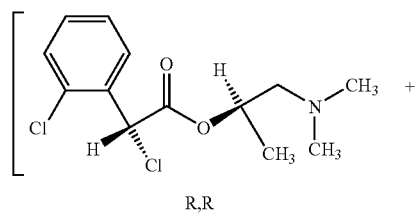

R,R

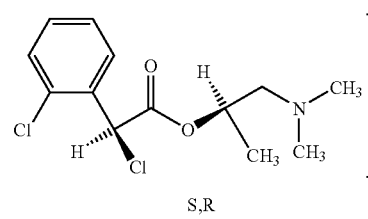

S,R may be determined by chiral HPLC, for example. Preferably, it is about 2:1 or more, more preferably 3:1 or more, especially about 4:1 or more.

The diastereomer mixture

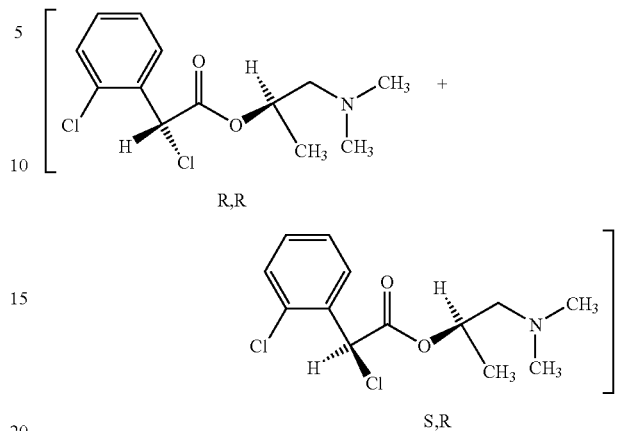

is preferably reacted with the compound of the formula (V)

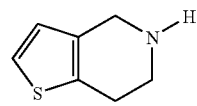 (V)

or the compound of the formula (VII)

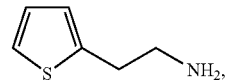 (VII)

preferably with the compound of the formula (V) without separation into the individual diastereomers.

For example, 4,5,6,7-tetrahydro-[3,2-c]-thienopyridine hydrochloride may be stirred with 2,α-dichlorophenylacetic acid-(R)-1-(dimethylamino)-2-propylester hydrochloride in a suitable solvent, especially a dipolar aprotic solvent, e.g. dimethyl formamide, DMSO or 1,3-dimethyl-3,4,5,6-tetrahydro-2-(1H)-pyrimidinone, in the presence of a suitable base, especially a carbonate, hydrogen carbonate or amine like triethyl amine and/or lithium carbonate, preferably at temperature in the range of 0 to 100° C. for a suitable period of usually several hours. In a particularly preferred embodiment, this reaction step is carried out in the presence of silica. It has been shown that this permits a further increase of the optical purity of the final product.

The product may be isolated by distribution between an organic layer and an aqueous layer and subsequent evaporation of the solvent. By conversion into the hydrochloride or the hydrobromide with the appropriate mineral acid, a crystalline salt may be obtained. The resulting mixture of diastereomers

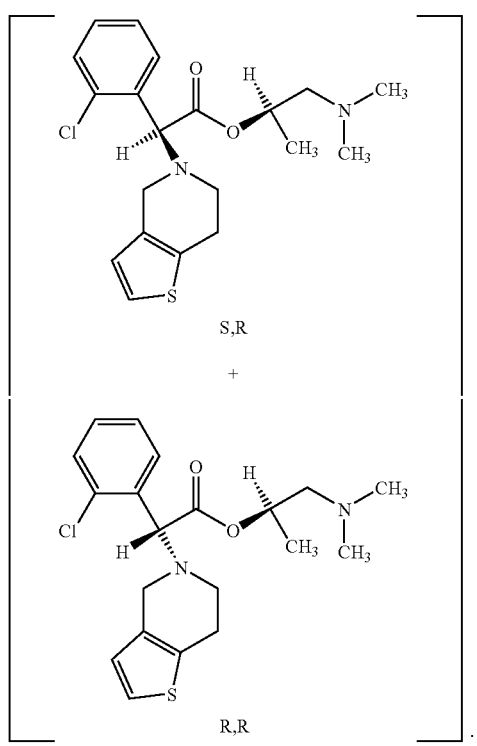

has an excess of the S,R-diastereomer of preferably 4:1 or more, more preferably about 9:1 or more.

Surprisingly, it has also been shown that a dicarboxylic acid instead of a mineral acid for converting the diastereomers into the corresponding salts may be used to great advantage. By using a dicarboxylic acid instead of the mineral acids the ratio of the desired diastereomer vis-à-vis the undesirable diastereomer may be further increased, and a mixture of diastereomers is obtained which contains 95% or more of the desired diastereomers and 5% or less of the undesirable diastereomer, especially those where the desired diastereomer is present in a ratio of 98% or more and the undesirable diastereomer in a ratio of 2% or less. Even diastereomer mixtures may be obtained which contain the desired diastereomer in a ratio of 99.5% or more and the undesirable diastereomer in a ratio of 0.5% or less.

The suitable dicarboxylic acids are not particularly limited, but maleic acid, oxalic acid and fumaric acid are preferred. Maleic acid is most preferred so that the second diastereomer mixture in the especially preferred embodiment of the invention is present as maleic acid salt.

If the mixture of diastereomers (diastereomer mixture 2) has a ratio of the (S,R)-enantiomer to the (R,R)-enantiomer which is still regarded as insufficient for the subsequent reaction to form Clopidogrel, the content of the desired (S,R)-diastereomer may be increased, for example by heating the mixture of diastereomers at reflux in a excess of a suitable polar-protic solvent, for example a suitable alcohol like isopropanol. In this manner, diastereomer mixtures may be obtained that contain the desired (S,R)-diastereomer in a ratio of 98% or more, especially 99.5% or more and, accordingly, contain the undesirable (R,R)-diastereomer in an amount of 2% or less, preferably 0.5% or less. By this process, other impurities of the diastereomer mixture may also be reduced.

The mixture of diastereomers

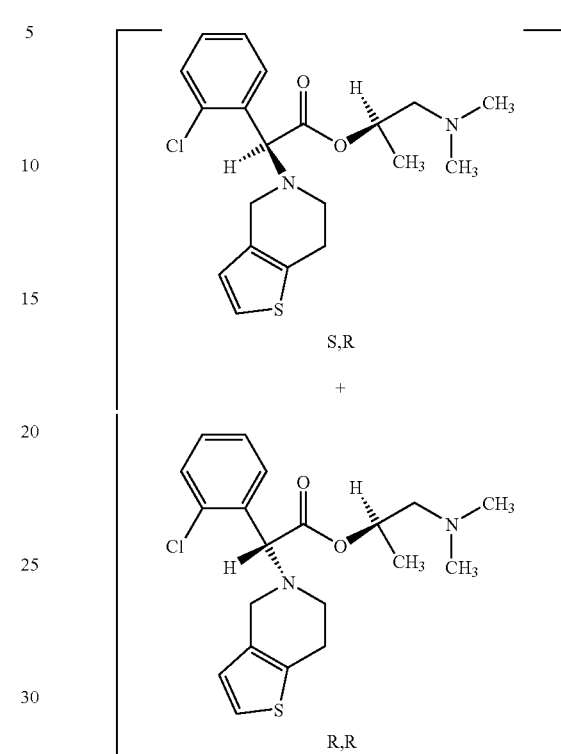

or the separated diastereomer

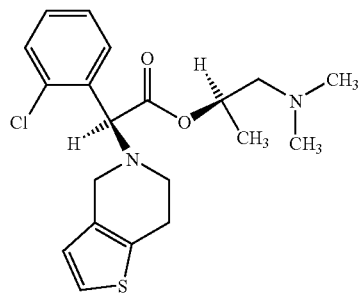

optionally as a salt, especially as the maleate salt, oxalate salt or fumarate salt, is converted by transesterification into the mixture of the S- and R-enantiomers of the Clopidogrel which is enriched with the S-enantiomer or is converted to pure Clopidogrel. For this purpose, the titanium or silica catalysts as described above are preferably used. As shown above, it is especially preferred to carry out the transesterification in a basic medium using a catalyst which preferably is the halide of a transition metal from the first or second subgroup of the periodic table of elements, such as $Cu_2X_2$, $CuX_2$, $AgX$, $AuX$, $AuX_3$, $CdX_2$, $Hg_2X_2$, $HgX_2$, $CoX_2$ or $ZnX_2$, especially $ZnX_2$ or $CoX_2$, X being a halide counterion, especially a chloride ion.

Transesterification is preferably conducted by heating of the compound of the formula

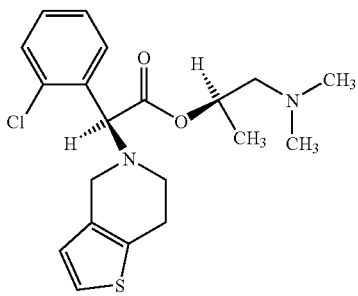

or of the diastereomer mixture

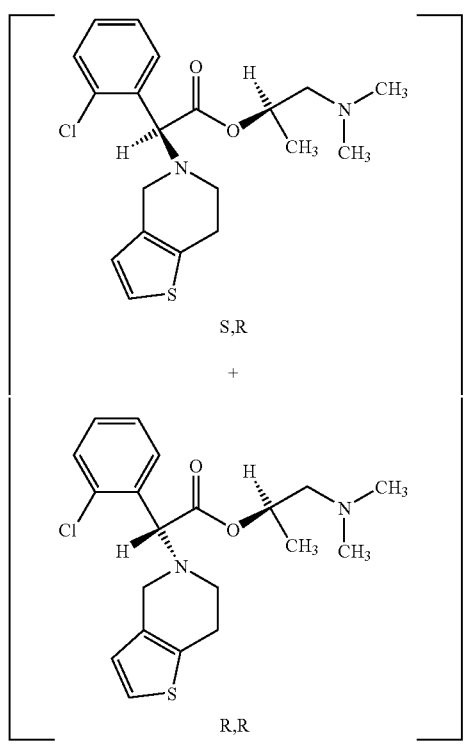

with the catalyst in methanol. The diastereomer mixture or, respectively, the separated compound as a free base or directly in the form of a salt, especially a salt with a dicarboxylic acid, most preferably as a maleate salt, may be used for the reaction. If the free base is used, the reaction rate is higher than in the case where the salt is used; however, the use of the salt results in particularly low racemisation during transesterification. The particularly preferred transesterification using a halide of a transition metal as described is preferably carried out under weakly alkaline conditions using a suitable anorganic or preferably organic base such as diisopropyl amine, triethyl amine or a pyrrolidine, for example N-methylpyrrolidine. If a salt of the diastereomer mixture used or if the preferred diastereomers used are employed for transesterification, it may be advantageous to use a stronger base such as triethyl amine or diisopropyl amine to increase the reaction rate, but this increases the risk of racemisation during transesterification. Therefore, it is preferred to use a suitable salt of the diastereomer mixture, said diastereomer mixture already being enriched to a point where it contains 95% or more, more preferably 98% or more, especially 99.5% or more of the desired diastereomer. Most preferably, the salt is an oxalate salt, a fumarate salt or maleate salt, especially a maleate salt, and the reaction is carried out under slightly alkaline conditions so that racemisation during transesterification is kept as low as possible.

After the reaction is completed, a base is added to the reaction mixture as shown in the examples, filtered off and worked up in the usual manner, again as shown in the examples. If the final product still contains the compound of the formula

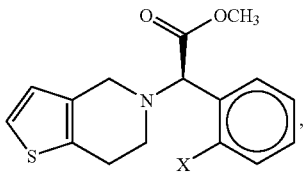

the desired Clopidogrel enantiomer may be separated in the usual manner. Again, reference is made to the citations quoted supra.

However, the undesirable Clopidogrel enantiomer is most preferably separated by dissolving the mixture of enantiomers in a suitable solvent, preferably a dipolar-aprotic solvent such as ketone, especially acetone, and acidifying the solution, for example with concentrated sulfuric acid. The racemic Clopidogrel hydrogen sulfate precipitates from the solution, and the desired enantiomer of the Clopidogrel remains in the mother liquor from which it may be recovered in great purity. If the content of the undesirable enantiomer is low, crystallisation of the racemic Clopidogrel hydrogen sulfate does not take place immediately after addition of the stoichiometric amount of sulfuric acid, and the amount of sulfuric acid must be increased. If this does not lead to immediate crystallisation either, seeding with racemic Clopidogrel hydrogen sulfate may be advisable.

Unless otherwise indicated in this description or self-evident from the context, "parts" and "percent" are always based on the weight.

The following examples illustrate the invention in greater detail.

EXAMPLE 1

2,α-Dichlorophenyl acetyl chloride

2-Chlorophenyl acetic acid (171 g) was added to 300 ml of thionyl chloride and the mixture stirred at 60° C. for 30 minutes. An iodine crystal followed by 300 ml of sulfuryl chloride was added in several portions. The mixture was heated at reflux for a total of 7 hours. Excess reagents were distilled off at reduced pressure. The residue (228 g) contained 82-84% of 2,α-Dichlorophenyl acetyl chloride, 5-6% of non-α-chlorinated 2-chlorophenyl acetyl chloride and about 10% of 2,4,(2,6),α-trichlorophenyl acetyl chloride. The crude acyl chloride was used in the subsequent reactions without further purification.

EXAMPLE 2

(R)-1-(Dimethylamino)-2-propanol ((R)-Dimepranol)

A solution of 190 g of dibenzoyl-L-tartaric acid in 1,200 ml of ethanol was mixed with 103 g of 1-(dimethylamino)-2-propanol. The resulting solution was acidified with 36 ml of 36% hydrochloric acid and seeded. After being left standing over night, the crystalline product was filtered off, washed with cold ethanol and diethyl ether and dried. Crude (R)-1-(dimethylamino)-2-propanol dibenzoyl-L-tartrate was recrystallised from 2,700 ml of hot ethanol, and the yield amounted to 187 g of pure diastereomeric salt. The salt was dissolved in 1000 ml of cold 20% sodium hydroxide solution and extracted in dichloromethane. The extract was dried, filtered, evaporated and the residual oil purified by distillation at atmospheric pressure. The product was distilled off at 122-124° C., and the yield was 46 g of (R)-Dimepranol (45% based on the starting racemate), $[\alpha_D^{20}]$ –27°.

EXAMPLE 3

2,α-Dichlorophenyl acetic acid-(R)-1-(dimethylamino)-2-propylester

2,α-Dichlorophenyl acetyl chloride (8.6 g) was dissolved in 30 ml of tetrahydrofurane, 1.2 g of 4-(dimethylamino)-pyridine was added and mixed. Then a solution of 4.1 g of (R)-Dimepranol in 30 ml of tetrahydrofurane was rapidly added with stirring and cooling. The crystalline aminoester hydrochloride was separated. The mixture was then heated to 55° C. and stirred at this temperature for 20 minutes, allowed to cool and then stirred at room temperature for a further 2 hours. Diethyl ether (2 ml) was added and the crystalline product filtered off, washed and dried at room temperature. Crude ester hydrochloride was recrystallised from isopropanol. The yield was 10.0 g. The purified ester hydrochloride was distributed between a saturated aqueous solution of sodium hydrogen carbonate and diethyl ether. After evaporation, the aminoester was obtained as a free base. The yield was 8.1 g (72.5%) of the, (R,R)-diastereomer being predominant (65-80%).

EXAMPLE 4

2,α-Dichlorophenylacetic acid-(R)-1-(dimethylamino)-2-propylester hydrochloride (Preferred Process)

2,α-Dichlorophenyl acetyl chloride (19.2 g, 86 mmol) was dissolved in 80 ml of tetrahydrofurane, and the solution added dropwise over 45 minutes with stirring and cooling to 10 to 15° C. in an ice water bath to a solution of 12 g (86 mmol) of (R)-1-(dimethylamino)-2-propanol hydrochloride in 80 ml of tetrahydrofurane which contained 12 ml (8.9 g, 88 mmol) of triethyl amine. The mixture was stirred at room temperature for three hours, and within two hours the crystalline hydrochloride of the amino ether precipitated. The mixture was heated at reflux for two hours. It was then cooled to 50° C., 60 ml of acetone were added and the mixture heated at reflux for another two hours. After cooling of the mixture, it was refrigerated over night (refrigerator). The crystalline product was filtered onto a glass frit under nitrogen and washed with 20 ml of acetone. Following that, it was dried at room temperature. A mixture of crude ester hydrochloride and triethylamine hydrochloride was obtained, which contained about 24 g of the diastereomeric ester. The content of the title compound in the mixture of the diastereomeric esters was determined by HPLC, and the mixture of the diastereomeric esters contained about 80% of the title compound which corresponds to a ratio of the desired R,R-diastereomer to the undesirable diastereomer of 4:1.

The diastereomer mixture thus obtained which contained the triethylamine hydrochloride was used for the subsequent process steps without further purification. Optionally, however, the mixture may also be purified by dissolving the crude mixture of the hydrochloride of the diastereomeric amino ester and the triethyl amine in the 2.5-fold amount (v/w) of boiling 2-propanol, adding the same volume of hot propyl acetate and cooling the mixture and leaving it in a refrigerator over night. The following day, the crystalline product may be filtered off under nitrogen, washed with 25 ml of cold (about 5° C.) 2-propyl acetate and dried.

EXAMPLE 5

1-Phenyl-2-(1-pyrrolidinyl)-ethanolhydrochloride

Water (10 ml) was added with stirring to a mixture of 24.0 g of styrene oxide and 21.3 g of pyrrolidine. The temperature of the mixture increased to almost 100° C. Water and excess pyrrolidine were distilled out of the resulting clear solution. The residue was dissolved in 60 ml of 1,2-dimethoxy ethane and the solution acidified with a 5.5 M solution of hydrogen chloride in 1,2-dimethoxy ethane. The precipitated hydrochloride salt was filtered off, washed with 1,2-dimethoxy ethane and dried. The filtrate was left standing in a refrigerator over night, and a second yield of the product was obtained. The total yield of crystalline 1-phenyl-2-(1-pyrrolidinyl)-ethanol hydrochloride was 35.9 g.

EXAMPLE 6

(R)-1-Phenyl-2-(1-pyrrolidinyl)-ethanol

Solutions of 35.8 g of di-O-benzoyl-L-tartaric acid in 150 ml methanol and 19.1 g of 1-phenyl-2-(1-pyrrolidinyl)-ethanol in 100 ml of methanol were mixed and the mixture left standing in a refrigerator for 2 days. The crystalline product was filtered off, washed with a small amount of cold methanol and diethyl ether and dried. The product was repeatedly recrystallised from hot ethanol, yielding an optically pure diastereomeric salt of 15.0 g. The free base was released by dissolving the salt in 100 ml of cold 20% aqueous sodium hydroxide and extracted in dichloromethane. After evaporation of the solvent, 7.2 g (38% based on the starting racemate) of the oily (R)-enantiomer of 1-phenyl-2-(1-pyrrolidinyl)-ethanol were obtained which solidified after storage in a refrigerator to become a crystalline mass. The product had a $[\alpha_D^{20}]$ value of –40° (methanol).

EXAMPLE 7

2,α-Dichlorophenyl acetic acid-(R)-2-(1-pyrrolidinyl)-1-phenylethyl ester

A solution of 5.7 g of (R)-1-phenyl-2-(1-pyrrolidinyl)-ethanol in 25 ml of tetrahydrofurane was added to a solution of 6.5 g of 2,α-dichlorophenyl acetyl chloride in 25 ml of tetrahydrofurane containing 0.9 g of 4-dimethylamine pyridine. According to a similar procedure as in example 3, a mixture of diastereomeric esters containing 72% (R,R) and 28% (R,S) of the product in a yield of 8.4 g (74%) was obtained.

EXAMPLE 8

2-Dimethylamino-1-phenyl ethanol

A solution of 12 g of sodium hydroxide in 60 ml of water was mixed with 100 ml of ethanol and 24.0 g of dimethylamine hydrochloride. Styrene oxide (24.0 g) was added and the mixture stirred at room temperature for two hours. The precipitated sodium chloride was filtered off, ethanol was evaporated at reduced pressure, and 8.0 g of sodium hydroxide were added to the remaining aqueous solution. The amino alcohol was extracted in diethyl ether, the extracts were dried and evaporated, and 26.7 g of an oily product was obtained which, according to the HPLC analysis, contained 87% of 2-dimethylamino-1-phenyl ethanol.

EXAMPLE 9

(R)-2-Dimethylamino-1-phenylethanol

Racemic 2-dimethylamino-1-phenyl ethanol was cleaved in accordance with the 2-pyrrolidinyl-1-phenyl ethanol (see example 6) using 16.5 g of crude amino alcohol as described in example 8. The yield of oily (R)-2-dimethylamino-1-phenyl ethanol with a $[\alpha_D^{20}]$ value of −45.5° (methanol) was 8.9 g.

EXAMPLE 10

2,α-Dichlorophenyl acetic acid-(R)-2-dimethylamino-1-phenylethyl ester

A mixture of diastereomeric esters wherein the (R,R)-esters were pre-dominant was prepared from 5.0 g of (R)-2-dimethylamino-1-phenyl ethanol as in example 3 and 7; the yield was 7.7 g.

EXAMPLE 11 trans-2-Dimethylaminocyclohexan-1-ol

The amino alcohol was prepared as described in example 8 using cyclohexene oxide (19.6 g) instead of styrene oxide. Oily trans-2-dimethylaminocyclohexan-1-ol was obtained in a yield of 22.0 g (76%).

EXAMPLE 12 trans-2-(S)-Dimethylamino-1-(R)-hydroxycyclohexane

The racemic amino alcohol of example 11 was cleaved according to examples 3, 5 and 8, using di-O-benzoyl-L-tartaric acid in a mole ratio of 1:1 (35.8 g di-O-benzoyl-L-tartaric acid and 14.5 g of racemic trans-2-dimethylaminocyclo-hexan-1-ol), employing acetone as the solvent. Oily trans-(S,R)-2-dimethylaminocyclohexan-1-ol was obtained in a yield of 5.2 g. The $[\alpha_D^{20}]$ value was −23° (methanol).

EXAMPLE 13

2,α-Dichlorophenyl acetic acid-trans-(S,R)-2-dimethylaminocyclohexyl ester

The ester of the trans-2-(S)-dimethylamino-1-(R)-hydroxycyclohexane with 2,α-dichlorophenyl acetic acid was obtained from 4.4 g of the amino alcohol and 6.5 g of acyl chloride in tetrahydrofurane in a yield of 6.7 g. According to HPLC analysis, the product contained 68% of the diastereomer of the ester of the α-(R)-chloric acid.

EXAMPLE 14

(S)-(2-Chlorophenyl)-4,5,6,7-tetrahydro-[3,2-c] thienopyridin-5-yl-acetic acid-(R)-1-(dimethylamino)-2-propylester dihydrochloride The free base of the 2,α-dichlorophenyl acetic acid-(R)-1-(dimethylamino)-2-propyl ester prepared as in example 3 (5.8 g) was dissolved in 30 ml of dimethylformamide and the solution mixed with 3.6 g of 4,5,6,7-tetrahydro-[3,2-c]-thienopyridine hydrochloride and 3.4 g of solid lithium hydrogen carbonate. The mixture was then stirred for 45 minutes at 80° C. After cooling to room temperature, the suspension was mixed with 100 ml of chloroform and 100 ml of water. The organic layer was separated and washed with water, dried and the chloroform was evaporated. The residue was dissolved in 40 ml of 2-propanol and decoloured with activated carbon. Gaseous hydrogen chloride (1.5 g) was introduced into the solution, and the crystalline hydrochloride salt precipitated. The salt was filtered off and washed with 10 ml of cold isopropanol. After drying, a product containing 85% of the desired (R,S) diastereomeric ester was obtained in a yield of 7.7 g (83%).

EXAMPLE 15

(S)-(2-Chlorophenyl)-4,5,6,7-tetrahydro-[3,2-c] thieno-pyridin-5-yl-acetic acid-(R)-1-(dimethylamino)-2-propylester dihydrobromide An approximately 3:1 mixture of the (R,S)- and (R,R)-diastereomers of the 2,α-dichlorophenylacetic acid-1-(dimethylamino)-2-propylester hydrochloride (20.0 g) was added with stirring in 4 portions to a suspension of 10.5 g 4,5,6,7-tetrahydro-[3,2-c]-thienopyridine hydrochloride in 150 ml of dimethylformamide containing 40 ml of triethyl amine. The mixture was heated to 45° C. and stirred at this temperature for 2 hours. Then, 150 ml of methyl-tert.-butyl ether and 300 ml of water were added and mixed thoroughly. The organic layer was separated and washed twice with water, dried and evaporated. A yield of 20.0 g of a mixture of the free bases of the diastereomeric aminoesters which contained 85% of the (R,S)-diastereomer (HPLC) was obtained. The residue was dissolved in a 15-fold excess in isopropyl acetate and the solution cooled to 5° C. in an ice bath. Gaseous hydrogen bromide was introduced into the mixture with stirring at 5-10° C. until 8.5 g of HBr had been absorbed. Stirring was continued for another two hours at 10° C. and then without cooling until room temperature was reached. The mixture was seeded and left standing in a refrigerator over night. The crystals of the aminoester dihydrobromide were filtered off, washed with cold isopropylacetate and dried. The yield was 20.2 g, and the (R,S)-diastereomer content was 92%.

EXAMPLE 16

Maleic acid salt of the (S)-(2-chlorophenyl)-4,5,6,7-tetrahydro-[3,2-c]thienopyridin-5-yl-acetic acid-(R)-1-(dimethylamino)-2-propylester (Preferred Process)

180 ml (191.4 g) of 1,3-dimethyl-3,4,5,6-tetrahydro-2-(1H)-pyrimidinone (in short: N,N'-dimethylpropylene urea), 18.0 g (100 mmol) of 4,5,6,7-tetrahydro-[3,2-c]thienopyridine hydrochloride, 60 ml (43.5 g, 425 mmol) of triethyl amine and 21 g (250 mmol) of lithiumcarbonate were introduced into a 1 liter flask. A crude product prepared according to example 4 and containing 31.38 g (96 mmol) of the amino ester was added with stirring. Then 12.0 g of silicon dioxide (Silica, 60 Å) were added. The mixture was heated to 35° C. and stirred at this temperature for 4 hours. After that, the temperature was raised to 50° C. and stirring was continued for another 30 minutes to complete the reaction. The mixture was cooled to room temperature, 300 ml of diisopropyl ether were added and the mixture was stirred for 15 minutes, followed by filtration over a glass frit. The silica and the solid salts were resuspended in 300 ml of diisopropyl ether (in a filter), and the solvent was drawn off. The filtrates were combined, extracted twice with 150 ml of water each and extracted twice with 150 ml of borate buffer, pH 6.5. The organic phase was separated and dried with anhydrous sodium sulfate. The drying agent was filtered off. Two washings with 15 ml of diisopropylether and evaporation followed. 37.4 g of the free base were obtained as an oily product. The purity of the product was determined to be 95% according to HPLC, and the product contained 82 to 85% of the desired (R,S)-diastereomer.

The crude product was heated carefully and mixed with a solution of 11.1 g (96 mmol) of maleic acid in 300 ml of 2-propanol. The mixture was heated to 50° C. with stirring until a clear solution was obtained. The mixture was then cooled to room temperature and stirred. The desired product crystallises after a short period of time. Stirring is continued for another 4 hours and the product separated on a sintered glass filter, washed twice with 10 ml of 2-propanol and then dried in air.

The yield was 38.8 g (97.5%, based on the content of the (S)-(2-chlorophenyl)-4,5,6,7-tetrahydro-[3,2-c]thienopyridin-5-yl acetic acid-(R)-1-(dimethylamino)-2-propyl ester in the crude starting product and 80%, based on the total amount of the diastereomer mixture in the starting product). The product had a melting point of 173° C. determined by DSC and contained more than 98% (HPLC) of the title compound. The content of the undesirable (R,R)-diastereomer was below 1%. The mother liquor and the wash solution contained both diastereomers in a ratio of 15:85. The ratio of the diastereomers was determined by chiral chromatography.

The content of the desired (R,S)-diastereomer in the final product was so high that it was possible to react the product directly without further purification and without further enrichment with the desired (R,S)-diastereomer to form Clopidogrel.

EXAMPLE 17

(2-Chlorophenyl)-α-2-[(2-thieno)ethyl]amino acetic acid-(R)-1-(dimethylamino)-2-propylester A solution of 2.9 g of 2,α-dichlorophenyl acetic acid-1-(dimethylamino)-2-propyl ester as the free base containing about 80% of (R,R)— and 20% of (R,S)-diastereomers in 20 ml of acetonitrile was mixed with 1.3 g of 2-thienylethyl amine and 4 ml of triethyl amine and the mixture heated at reflux with stirring for 2 hours. Acetonitrile and excess triethyl amine were evaporated and the residue was divided between chloroform and water. The organic phase was separated, washed with water, dried, and the solvent evaporated. The residue (3.2 g) contained a mixture of 85% of (R,S)- and 15% of (R,R)-diastereomeric esters which was used for the next step without further purification.

EXAMPLE 18

(2-Chlorophenyl)-α-4,5,6,7-tetrahydro-[3,2-c]thienopyridin-5-yl-acetic acid-(R)-1-(dimethyl-amino)-2-propylester dihydrobromide A crude mixture of diastereomeric (R,S)- and (R,R)-α-(2-chlorophenyl)-α-2-[(2-thieno)ethyl]amino acetic acid-(1-(dimethylamino)-2-propyl ester (3.1 g) prepared as in example 17 was taken up in 10 ml of 2 M hydrochloric acid, and 5 ml of 36% aqueous formaldehyde was added with stirring. The mixture was stirred for 2 hours at 50° C. The reaction mixture was distributed between diisopropylether and 10% aqueous sodium hydrogen carbonate. The organic layer was separated, washed with water, dried and evaporated under reduced pressure. The residue was dissolved in 30 ml of a 1:1 mixture of 2-propanol and 2-propyl acetate. Gaseous hydrogen bromide (1.6 g) was introduced into the mixture with stirring and cooling to 10° C. The precipitated salt was filtered off, washed with 2-propyl acetate and dried, and 2.85 g of a crystalline product which contained about 92% of (R,S)- and 8% of (R,R)-Diastereomer (chiral HPLC) were obtained.

EXAMPLE 19

Transesterification of the hydrochloride of the (S)-(2-chlorophenyl)-4,5,6,7-tetrahydro-[3,2-c]thienopyridin-5-yl-acetic acid-(R)-1-(dimethylamino)-2-propyl ester by catalysis with ortho-titanate Ethylene glycol (1.36 g) was added to 12.6 g of titanium (IV) isopropoxide and both components were mixed thoroughly. An exotherm reaction then followed, forming ethylene-bis-(triisopropyl)ortho-titanate which was used as transesterification catalyst after the mixture had cooled. The catalyst was added to a solution of 7.43 g (S)-(2-chlorophenyl)-4,5,6,7-tetrahydro-[3,2-c]-thienopyridin-5-yl-acetic acid-(R)-1-(dimethylamino)-2-propylester hydrochloride in 70 ml of methanol, the mixture heated at reflux for 48 hours and then allowed to cool to room temperature. Sodium hydrogen carbonate (6.3 g) was then added and the mixture stirred for 30 minutes. The solids were filtered off and the filtrate evaporated. The residue was suspended in 200 ml of diethyl ether and the suspension stirred for 30 minutes. The catalyst was decomposed by the slow addition of 1.6 ml of water. Solid anhydrous sodium sulfate (10 g) was added to the suspension of a bulky white precipitate of the hydrogenated titanium oxide formed, and the mixture was stirred for a further 20 minutes. The solids were then filtered off and washed on the filter with several portions of diethyl ether. The filtrates and water used for washing were evaporated and 3.9 g of Clopidogrel were obtained as a free base containing about 15% of the (R)-enantiomer and 85% of the (S)-enantiomer.

EXAMPLE 20

Transesterification of (S)-(2-chlorophenyl)-4,5,6,7-tetrahydro-[3,2-c]thienopyridin-5-yl acetic acid-(R)-1-(dimethylamino)-2-propylester by catalysis with chlorinated silica Dried silica (120° C., 20 torr, 2 hours) with an average pore diameter of 60 Å (20 g) was suspended in 60 ml of thionyl chloride and the suspension heated at reflux for 46 hours. The modified silica was filtered off, dried for 2 hours in a vacuum dryer at 125° C. under reduced pressure and then activated by heating to 360° C. for 30 minutes. The free base of the (S)-(2-chlorophenyl)-4,5,6,7-tetrahydro-[3,2-c]thienopyridin-5-yl acetic acid-(R)-1-(dimethylamino)-2-propyl ester (10.0 g) was dissolved in 150 ml of methanol. Then 20 g of activated modified silica were added and the mixture heated at reflux with stirring for 48 hours. The silica was filtered off, washed with 100 ml of methanol in several portions, and the combined filtrates and the water used for washing evaporated. The evaporation residue (10.0 g containing 7.1 g of (S)-Clopidogrel) was converted to a pharmaceutically acceptable salt of the (S)-Clopidogrel.

EXAMPLE 21

Transesterification of the dihydrochloride of the (S)-(2-chlorophenyl)-4,5,6,7-tetrahydro-[3,2-c]thienopyridin-5-yl acetic acid-(R)-1-(dimethylamino)-2-propyl ester by catalysis with chlorinated silica Dried silica (120° C., 20 torr, 2 hours) with an average pore diameter of 100 Å (20 g) was suspended in a solution of 14 g of phosphorus pentachloride in 80 ml of hexane and heated at reflux for 10 hours. After cooling, the suspension was allowed to stand over night, then filtered off, washed twice with 20 ml of hexane and dried for two hours under a nitrogen stream. This was followed by drying for 2 hours in a vacuum dryer at 120° C. and at reduced pressure. Then the catalyst was activated by 30 minutes heating to 360° C. The catalyst retains its performance over several months if it is kept in a sealed container.

(S)-(2-Chlorophenyl)-4,5,6,7-tetrahydro-[3,2-c]thienopyridin-5-yl acetic acid-(R)-1-(dimethyl-amino)-2-propylester dihydrochloride (10.0 g) was dissolved in 150 ml of methanol. 20 g of activated modified silica were added, and the mixture was heated for 46 hours with stirring at reflux. The silica was filtered off, washed with three 25 ml loads of methanol and the combined filtrates and the water used for washing evaporated. The remaining product was divided between a cold saturated aqueous solution of sodium hydrogen carbonate and tethyl-tert.butylether. The organic layer was separated, and the released Dimepranol was extracted in water. After evaporation of the methyl-tert.butylether from the organic phase, the residue contained 6.5 g of (S)-Clopidogrel, free base, which was converted to a pharmaceutically acceptable salt and purified by crystallisation.

EXAMPLE 22

(S)-Clopidogrel

Purification and Enantiomeric Enrichment of the Transesterification Product

Variant A

The crude free base of the Clopidogrel which was obtained after trans-esterification (16.0 g) and which contained 8% of the (R)-enantiomer and 92% of the (S)-enantiomer was dissolved in 240 ml of acetone. The solution was cooled to 15° C., and 0.43 ml (0.78 g) of 96% sulfuric acid in 10 ml of acetone was added with stirring. After about 2.5 hours, crystals of the racemic Clopidogrel sulfate dihydrate were formed which were filtered off while the (S)-enantiomer remained in solution. The filtrate was evaporated under reduced pressure, and the residue was divided between methyl-tert.butylether and saturated aqueous sodium hydrogen carbonate solution. The organic layer was dried and evaporated. (S)-Clopidogrel was obtained as the free base with an optical purity of 99.0% in a yield of 11.2 g.

EXAMPLE 23

(S)-Clopidogrel

Purification and Enantiomeric Enrichment of the Transesterification Product

Variant B

The purification of the transesterification product was carried out as in example 20 except that triethyl amine or another suitable volatile tertiary amine was added in the amount corresponding to the enantiomeric excess of (S)-Clopidogrel before precipitation of the racemic Clopidogrel sulfate. The amine forms a double sulfate salt with (S)-Clopidogrel with increased solubility which contributes to the increase of the optical purity of the product. The volatile amine may be removed easily after the decomposition of the salt, the extraction of the free base into an organic solvent and evaporation.

EXAMPLE 24

Preparation of Clopidogrel

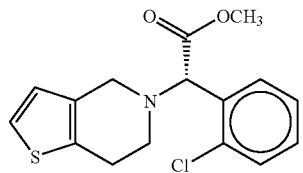

by transesterification of the maleate of the (S)-(2-chlorophenyl)-4,5,6,7-tetrahydro-[3,2-c]thienopyridin-5-yl acetic acid (R)-1-(dimethylamino)-2-propylester by catalysis with zinc chloride in a basic medium (preferred process)

25.2 g (0.185 mol) of anhydrous zinc chloride and 27 ml (21.6 g, 0.25 Mol) N-methylpyrrolidine were dissolved in 550 ml of hot methanol (maximum water content 0.1%). 65 g (0.128 mol) of the product prepared according to example 16 having a content of (S)-(2-chlorophenyl)-4,5,6,7-tetrahydro-[3,2-c]thienopyridin-5-yl acetic acid-(R)-1-(dimethylamino)-2-propylester-maleate salt of approx. 98.0% and a content of the corresponding (R,R)-enantiomer of approx 0.5% (the remaining 1.5% being undetermined impurities) were added to the solution at reflux. The mixture was heated until reflux on a water bath until the reaction was substantially completed (transesterification of 97.5 to 98.5% as determined by HPLC). After completion of the transesterification, the mixture was cooled, the methanol removed at reduced pressure in a rotatory evaporator and the residue mixed with 160 ml of a 10% aqueous sodium hydrogen carbonate solution and 200 ml of diisopropyl ether. 25% aqueous ammonia was added gradually until the suspension of zinc hydroxide and basic zinc carbonate was dissolved (approx. 70 ml). The organic phase was separated, and the aqueous phase extracted twice with 40 ml of diisopropyl ether. During the extraction, the temperature was held at 12 to 15° C., and the Clopidogrel content in the aqueous layer monitored by HPLC. The organic layers were combined and washed three times with 60 ml of saline. The organic layer was dried over sodium sulfate, filtered and evaporated. The yield of crude Clopidogrel base was quantitative (41 g).

The Clopidogrel thus obtained contained 93 to 96% of the desired S-(+)-Clopidogrel and 4 to 7% of the undesirable S-(−)-Clopidogrel. It was dissolved in 4 to 8 ml/g of acetone and 20% of its molar equivalent in concentrated sulfuric acid was gradually added with cooling (15° C.). The racemic Clopidogrel hydrogen sulfate precipitated slowly from the solution. The reaction mixture was stirred over night and the racemic solid separated by filtration. The desired S-(+)-enantiomer of the Clopidogrel hydrogen sulfate remained in the mother liquor. Its concentration was adjusted to about 25%, and the dropwise addition of concentrated sulfuric acid up to a content of 1.05 equivalents was continued with cooling. After the solution had been seeded with the desired S-(+)-enantiomer of the Clopidogrel, crystallisation occurred rapidly. The mixture was stirred at room temperature for 5 or 6 hours and then filtered through a sinter filter S2, washed with 50 ml of acetone and then dried, first in air and then in a vacuum dryer at 50° C. and 22 torr. If clouding occurs at the beginning of the sulfuric acid addition which then agglomerates into a brown amorphous solid, this amorphous material must be removed from the reaction mixture. It consists of amorphous sulfates of impurities or of the starting products which would affect the subsequent crystallisation of the polymorphous hydrogen sulfate.

The yield of the process was 78 to 63% (based on pure starting material). The melting point was 182 to 184° C., and the content of the undesirable R-(−)-Clopidogrel was 0.5 to 1.2%.

The invention claimed is:

1. A process for preparing (R)-1-(dimethylamino)-2-propanol ((R)-Dimepranol)) of the formula:

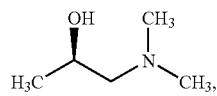

said process comprising the steps of first contacting a mixture of the compounds of the formula:

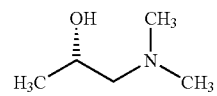

and

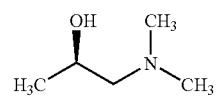

with L-(−)-di-O-benzoyl-L-(−)-tartaric acid (L-(−)-DBTA) to form a salt of the latter with (R)-dimepranol and then contacting the solution with an achiral mineral acid followed by the separation of the L-(−)-DBTA-salt of the compound

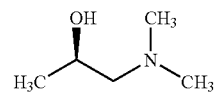

* * * * *